US012121379B2

(12) United States Patent
Baxter, III et al.

(10) Patent No.: US 12,121,379 B2
(45) Date of Patent: Oct. 22, 2024

(54) LEAD ORIENTATION DETECTION

(71) Applicant: Medtronic, Inc., Minneapolis, MN (US)

(72) Inventors: Walton W. Baxter, III, San Clemente, CA (US); Mark J. Conroy, St. Louis Park, MN (US); Tyler S. Stevenson, Westminster, CO (US)

(73) Assignee: Medtronic, Inc., Minneapolis, MN (US)

( * ) Notice: Subject to any disclaimer, the term of this patent is extended or adjusted under 35 U.S.C. 154(b) by 458 days.

(21) Appl. No.: 17/463,009

(22) Filed: Aug. 31, 2021

(65) Prior Publication Data

US 2022/0061784 A1 Mar. 3, 2022

Related U.S. Application Data

(60) Provisional application No. 63/072,702, filed on Aug. 31, 2020.

(51) Int. Cl.
*A61B 6/12* (2006.01)
*A61B 6/03* (2006.01)
*A61B 90/00* (2016.01)
*A61N 1/05* (2006.01)

(52) U.S. Cl.
CPC ............... *A61B 6/12* (2013.01); *A61B 6/032* (2013.01); *A61B 90/39* (2016.02); *A61N 1/05* (2013.01); *A61B 2090/3966* (2016.02)

(58) Field of Classification Search
CPC ........... A61B 6/12; A61B 6/032; A61B 90/39; A61B 2090/3966; A61B 2034/2065; A61B 34/20; A61B 6/501; A61N 1/05; A61N 1/372; G06T 2207/30052; G06T 7/73; G06T 2207/10081
See application file for complete search history.

(56) References Cited

U.S. PATENT DOCUMENTS

| | | | |
|---|---|---|---|
| 6,542,773 B2 * | 4/2003 | Dupree | A61B 5/7445 600/509 |
| 8,995,731 B2 | 3/2015 | Joglekar | |
| 9,549,172 B2 * | 1/2017 | Kim | H04N 13/315 |
| 10,265,531 B2 | 4/2019 | Bokil | |
| 10,525,257 B2 | 1/2020 | Govea et al. | |
| 10,631,937 B2 | 4/2020 | Tyulmankov et al. | |

(Continued)

OTHER PUBLICATIONS

Lee, E. "Improving MR Image Quality in Patients with Metallic Implants" RadioGraphics, vol. 41, Issue 4, pp. 945-1264 E126-E137 (Year: 2021).*
Bokil et al., "EP 53: Determining the Orientation of Directional Deep Brain Stimulation Leads From Computed Tomography Data," Clinical Neurophysiology, vol. 127, Issue 9, Sep. 2016, p. e198.

(Continued)

*Primary Examiner* — Mia M Thomas
(74) *Attorney, Agent, or Firm* — Shumaker & Sieffert, P.A.

(57) ABSTRACT

Devices, systems, and techniques are disclosed for determining an orientation of an implanted medical lead. For example, a system may include processing circuitry configured to receive image data representing a lead implanted within a patient, identify, from the image data, at least one hypointensive portion, identify, from the image data, at least one hyperintensive portion, determine, based on the at least one hypointensive portion and the at least one hyperintensive portion, an orientation of the lead within the patient, and output the orientation of the lead.

25 Claims, 13 Drawing Sheets

(56) References Cited

U.S. PATENT DOCUMENTS

| | | | | |
|---|---|---|---|---|
| 10,661,074 | B2* | 5/2020 | Goetz | A61N 1/36157 |
| 10,959,672 | B2 | 3/2021 | Souza et al. | |
| 11,090,494 | B2* | 8/2021 | Stone | G06F 3/04815 |
| 2009/0281417 | A1* | 11/2009 | Hartmann | A61B 34/20 600/424 |
| 2010/0030063 | A1* | 2/2010 | Lee | A61B 5/06 600/424 |
| 2010/0284593 | A1* | 11/2010 | Delsanto | G06T 7/0012 382/130 |
| 2017/0136238 | A1* | 5/2017 | Hartig | A61B 5/00 |
| 2018/0008820 | A1* | 1/2018 | Goetz | A61N 1/0534 |
| 2018/0307310 | A1* | 10/2018 | McCombe | G06F 3/012 |
| 2019/0192229 | A1* | 6/2019 | Berlin | A61B 8/5246 |
| 2020/0230397 | A1 | 7/2020 | Li et al. | |
| 2020/0237326 | A1 | 7/2020 | Achatz et al. | |
| 2020/0337636 | A1* | 10/2020 | Souza | A61N 1/05 |
| 2022/0184401 | A1* | 6/2022 | Vaidyanathan | A61N 1/36139 |
| 2022/0202491 | A1* | 6/2022 | Pathak | A61B 5/055 |
| 2023/0120840 | A1* | 4/2023 | Stevenson | G06T 7/74 382/128 |

OTHER PUBLICATIONS

Hellerbach et al., "DiODe: Directional Orientation Detection of Segmented Deep Brain Stimulation Leads: A Sequential Algorithm Based on CT Imaging," Stereotactic and Functional Neurosurgery, vol. 96, Nov. 27, 2018, pp. 335-341.

Hunsche et al., "Determining the Rotational Orientation of Directional Deep Brain Stimulation Leads Employing Flat-Panel Computed Tomography," Operative Neurosurgery, vol. 16, No. 4, Apr. 2019, pp. 465-470.

Motevakel et al., "Localization of Deep Brain Stimulation Electrodes via Metal Artifacts in CT Images," 2014 36th Annual International Conference of the IEEE Engineering in Medicine and Biology Society, vol. 127, Aug. 26-30, 2014, pp. 1055-1058.

Reinacher et al., "Determining the Orientation of Directional Deep Brain Stimulation Electrodes Using 3D Rotational Fluoroscopy," American Journal of Neuroradiology, vol. 38, Issue 6, May 2017, pp. 1111-1116.

Sitz et al., "Determining The Orientation Angle of Directional Leads For Deep Brain Stimulation Using Computed Tomography and Digital X-Ray Imaging: A Phantom Study," Medical Physics, vol. 44, No. 9, Sep. 2017, pp. 4463-4473.

U.S. Appl. No. 17/934,805, filed Sep. 23, 2022, naming inventors Stevenson et al.

* cited by examiner

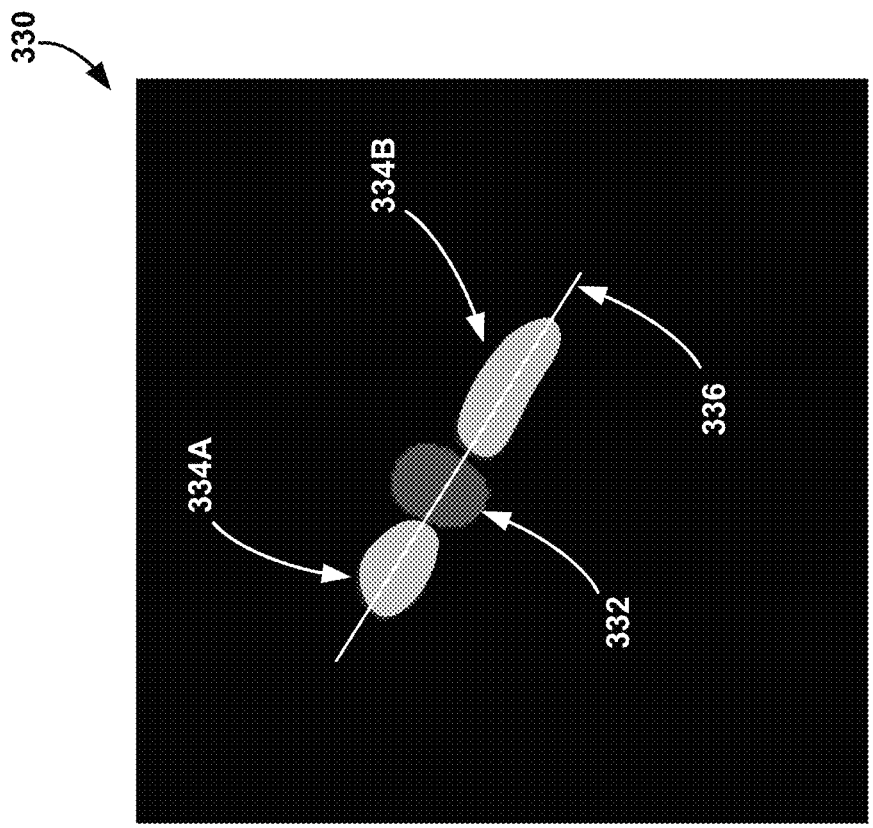
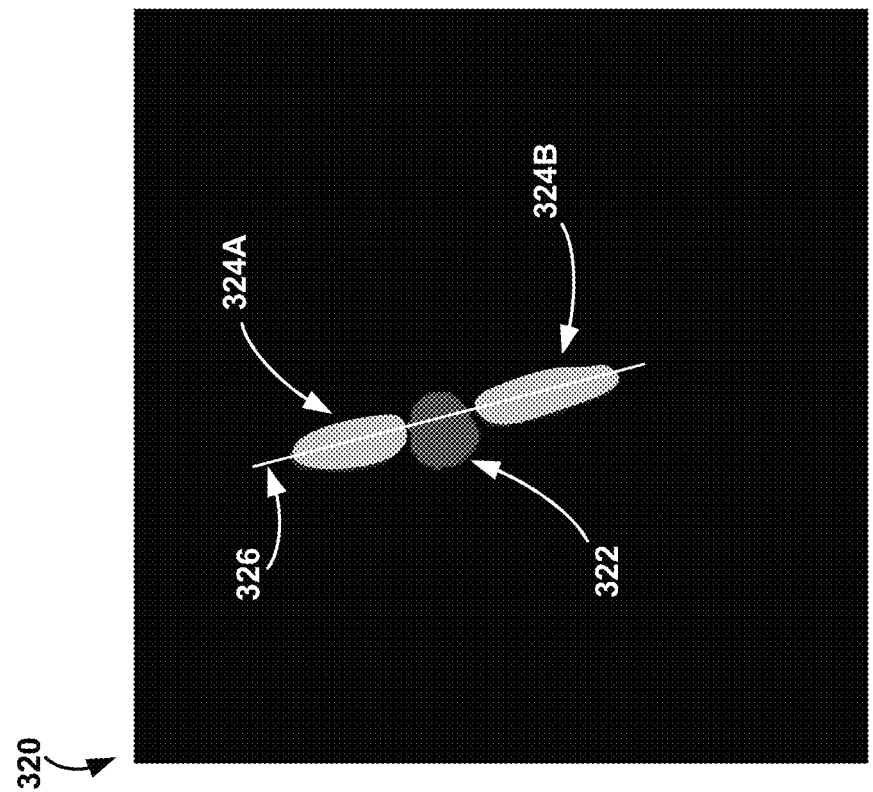
FIG. 8B
FIG. 8A

LEAD ORIENTATION DETECTION

This application claims the benefit of U.S. Provisional Patent Application No. 63/072,702, filed Aug. 31, 2020, the entire contents of which is incorporated herein by reference.

TECHNICAL FIELD

This disclosure generally relates to medical devices, and more specifically, detecting orientation of medical leads.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agents, insulin, pain relieving agents or anti-inflammatory agents to a target tissue site within a patient. In some systems, an implantable electrical stimulator delivers electrical therapy to a target tissue site within a patient with the aid of one or more electrodes, which may be deployed by medical leads and/or on a housing of the electrical stimulator, or both.

During a programming session, which may occur during implant of the medical device, during a trial session, or during an in-clinic or remote follow-up session after the medical device is implanted in the patient, a clinician may generate one or more therapy programs (also referred to as therapy parameter sets) that are found to provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. In examples in which electrical stimulation is delivered in the form of electrical pulses, for example, the therapy parameters may include an electrode configuration including an electrode combination and electrode polarities, an amplitude, which may be a current or voltage amplitude, a pulse width, and a pulse rate.

SUMMARY

In general, the disclosure describes devices, systems, and techniques for determining an orientation of an implanted lead with respect to tissue. For example, an implantable medical device (IMD) may be coupled to one or more leads carrying respective electrodes. These electrodes may be disposed at different locations around the perimeter of the lead which enables directional stimulation and/or sensing via the lead. Once implanted, a lead detection system may determine the orientation of the lead, and this the electrodes carried on the lead, with respect to the anatomy of the patient.

For example, the system may receive image data of the patient's anatomy and the implanted lead. In one example the image data may be or include computed tomography (CT) image data. Hyperintensive portions within the CT image data may be indicative of radiopaque structures, such as metal, located within the patient. Hypointensive portions within the CT image data may be artifacts in the CT image data caused by one or more objects within the patient, such as a radiopaque orientation marker or an electrode carried by the lead. The system may identify one or more hyperintensive portions within the CT image and one or more hypointensive portions within the CT image and determine the orientation of the lead based on the spatial relationship between the hyperintensive and hypointensive portions. A hypointensive portion may generally have a relatively low intensity of pixels or voxels in the CT image data, which is in contrast with a hyperintensive portion that may generally have a relatively high intensity of pixels of voxels in the CT image data.

In one example, a system includes processing circuitry configured to receive computed tomography (CT) image data representing a lead implanted within a patient, identify, from the CT image data, at least one hypointensive portion, identify, from the CT image data, at least one hyperintensive portion, determine, based on the at least one hypointensive portion and the at least one hyperintensive portion, an orientation of the lead within the patient, and output the orientation of the lead.

In another example, a method includes receiving computed tomography (CT) image data representing a lead implanted within a patient, identifying, from the CT image data, at least one hypointensive portion, identifying, from the CT image data, at least one hyperintensive portion, determining, based on the at least one hypointensive portion and the at least one hyperintensive portion, an orientation of the lead within the patient, and outputting the orientation of the lead.

In another example, a computer-readable storage medium stores instructions that, when executed, cause processing circuitry to receive computed tomography (CT) image data representing a lead implanted within a patient, identify, from the CT image data, at least one hypointensive portion, identify, from the CT image data, at least one hyperintensive portion, determine, based on the at least one hypointensive portion and the at least one hyperintensive portion, an orientation of the lead within the patient, and output the orientation of the lead.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 8A and 8B are example thresholded representations of the hypotensive and hypertensive portions of the CT images of FIGS. 7A and 7B.

DETAILED DESCRIPTION

Figure 1:
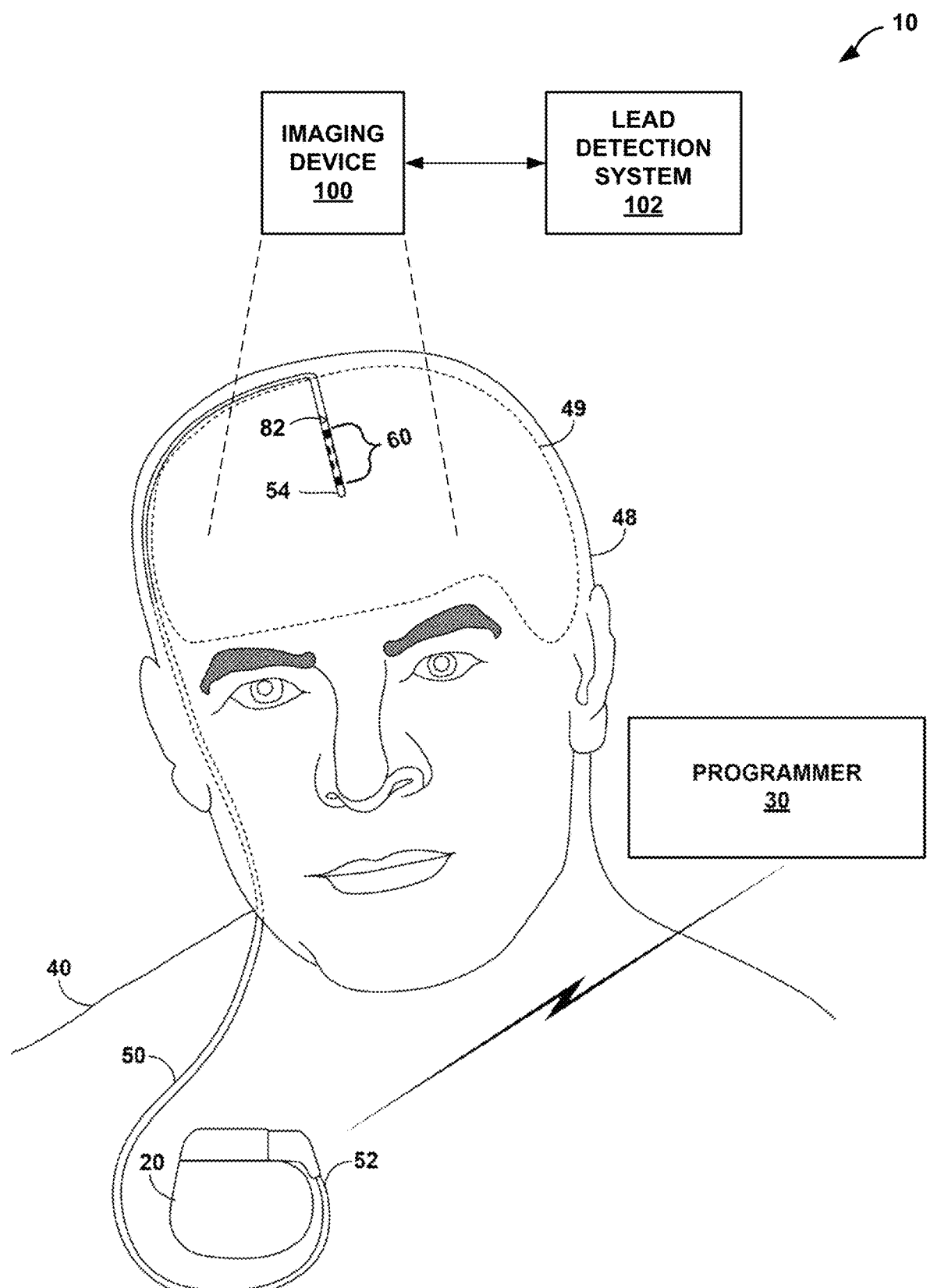
FIG. 1 is a conceptual diagram illustrating an example deep brain stimulation (DBS) system configured to detect a lead configured to deliver electrical stimulation therapy to a tissue site within a brain of a patient.

In general, the disclosure is directed to devices, systems, and methods for determining an orientation and/or position of a lead implanted in a patient. A lead may include one or more electrodes that are used to deliver electrical stimulation therapy to the patient. Some electrodes, such as ring electrodes disposed completed around a perimeter of a lead housing, may deliver electrical stimulation therapy radially in all directions about a longitudinal axis of the lead. Other electrodes, such as partial ring or segmented electrodes, are located at a specific portion of the perimeter of the lead. In this manner, these electrodes located at a specific perimeter or circumferential position may be referred to as directional electrodes in that they enable the delivery of electrical stimulation therapy radially in only certain directions about the longitudinal axis of the lead that correspond with the position of the partial ring or segmented electrode. The rotational orientation of the lead (i.e., to enable the targeting of specific tissue) may be important to effective programming a stimulator to deliver therapy using leads with electrodes having complex geometry (e.g., electrodes at different locations around a perimeter of the lead). However, a clinician may not be able to implant a lead while maintaining a specific rotational orientation and/or the leads may rotate about the longitudinal axis after initial insertion (e.g., upon securing the lead and/or over time being implanted within the patient). In this manner, the physician may need to program the lead without knowing the orientation of the lead (e.g., rotational orientation and/or longitudinal orientation) with respect to anatomical tissue of the patient.

In accordance with one or more techniques of this disclosure, a system may utilize data from an imaging modality (e.g., CT image data or image data from a different imaging modality) of a patient to determine an orientation and/or a location of a lead implanted in the patient. In the example of the CT imaging modality, the system may receive CT image data of the patient's anatomy and the implanted lead. The system may analyze the CT image data and identify hypointensive and/or hyperintensive portions within the CT image data. The hypointensive portions include low intensity values of the CT image data, whereas hyperintensive portions include high intensity values. For example, in the context of CT image data in which intensity is identified by Hounsfield Units (HU), a hypointensive portion include a low value of HU and a hyperintensive portion includes high value of HU. In this manner, the hyperintensive portions within the CT image data may be indicative of radiopaque structures, such as metal, bone, etc. located within the patient. Hypointensive portions within the CT image data may be artifacts in the CT image data caused by one or more objects within the patient, such as a radiopaque orientation marker or an electrode carried by the lead. In other words, the artifacts may have a low intensity that is a lower intensity value than soft tissue that are relatively transmissive to x-rays. The artifacts that are hypointensive may be indicative of no tissue or fluid absorbing x-rays due to the low intensity, but the artifacts of low intensity are caused by the computation of the CT image data and influenced by the pixels or voxels of high intensity. The artifacts may be caused by the generation of the CT image data in some examples. Using this CT image data, the system may identify one or more hyperintensive portions within the CT image and one or more hypointensive portions within the CT image and determine the orientation of the lead based on the spatial relationship between the hyperintensive and hypointensive portions. For imaging modalities other than CT, artifacts present within other image data (e.g., MM image data) may be associated with implanted devices and similarly be used to identify the orientation of an implanted device within the patient.

In some examples, one or more hyperintensive portions and one or more hypointensive portions may be associated with an orientation marker of the implanted lead. The lead may include various features to facilitate the determination of the lead orientation. For instance, the lead may include one or more orientation markers at specific positions. These orientation markers may be radiopaque and configured (e.g., shaped and/or made from certain materials) to be detectable in the imaging data. The orientation marker may include one or more portions that are located at one position around the perimeter of the lead instead of a different position around the perimeter of the leads. In some cases, the orientation marker may be indicated by a hyperintensive portion due to the metal of the orientation marker, and one or more hypointensive portions extend out from the hyperintensive portion. The system may determine the rotational, or circumferential, orientation of the lead based on the location of the one or more hypointensive portions.

In some examples, the system may identify multiple orientation markers located at respective different axial slices of the CT image data, and determine the orientation of the lead based on the circumferential orientation of hypointensive portions with respect to hyperintensive portions within each axial slice. For example, the orientation markers may be disposed at a non-orthogonal angles with respect to each other (e.g., a 60 degree offset). The system may determine a respective axis through the hypointensive and hyperintensive portions within each axial slice and determine the circumferential orientation of the lead according to the axes within the axial slices. In other examples, the system may determine similar lead orientations based on a single orientation marker and/or one or more levels of electrodes. For example, the system may identify one or more hyperintensive portions and hypointensive portions associated with the electrodes at a common axial location of the lead and determine the location of the electrodes based on the spatial relationship between the hyperintensive portions and the hypointensive portions. In any case, the CT image data may be registered to an anatomical direction of the patient so that the orientation of the lead can be mapped to the anatomical orientation of the patient.

The system may provide the results (i.e., the predicted orientation and/or positions of the electrodes) to a practitioner (e.g., a physician, a physician's assistant, or other clinician). As one example, the system may output, for display, a graphical indication (e.g., a visualization) of the lead as-implanted within the patient. For instance, the system may output a graphical representation of the lead as-implanted overlaid on an image of the patient (e.g., the lead may be shown with respect to various anatomical landmarks). This lead over image technique may enable a clinician to relate the electrode orientation to an anatomic stimulation target. In another example, the system may output, for display, the CT image data including the hypointensive and hyperintensive portions with or without a representation of the lead overlaid on the CT image data showing the orientation of the lead. As another example, the system may output a differential angle that represents a difference between a target orientation and the determined orientation.

The various systems, devices, and techniques described herein may provide one or more advantages of other approaches. For example, the system as described herein may determine the rotational, or circumferential, orientation of the lead with respect to patient tissue. This lead orientation can then be leveraged by the system and the clinician to appropriately program one or more sensing vectors or stimulation therapy with electrodes at known locations with respect to one or more anatomical structures of the patient. This process may result in more efficacious therapy and lower risks of side effects. In addition, the techniques described herein may be less sensitive to noisy CT data or techniques that rely only on identification of the hyperintensive portions of CT data indicative of the radiopaque lead elements of interest. For example, an orientation marker may be unsymmetrical around the perimeter of the lead to facilitate identification via CT imaging. However, it may be difficult to identify relatively small features of the orientation marker because the large intensity of the radiopaque marker obscures finer detail. The hypointensive portions may be artifacts within the CT image data that correspond to radiopaque marker geometry and facilitate the identification of the spatial orientation of the marker or other feature of the lead.

FIG. 1 is a conceptual diagram illustrating an exemplary system 10 including lead 50 implanted in the brain 49 of patient 40. Although only one lead 50 is shown for illustration, two or more leads may be implanted in brain 49, and system 10 may determine the orientation of each lead implanted in patient 40. For ease of illustration, examples of the disclosure will primarily be described with regard to implantable electrical stimulation leads and implantable medical devices that apply neurostimulation therapy to brain 49 of patient 40 in the form of deep brain stimulation (DBS). However, the features and techniques described herein may be useful in other types of medical device systems which employ medical leads to deliver electrical stimulation to a patient and/or sense electrical signals via one or more electrodes of the lead. For example, the features and techniques described herein may be used in systems with medical devices that deliver stimulation therapy to a patient's heart, e.g., pacemakers, and pacemaker-cardioverter-defibrillators. As other examples, the features and techniques described herein may be embodied in systems that deliver other types of neurostimulation therapy (e.g., spinal cord stimulation or vagal stimulation), stimulation of at least one muscle or muscle groups, stimulation of at least one organ such as gastric system stimulation, stimulation concomitant to gene therapy, and, in general, stimulation of any tissue of a patient. The medical lead system may be used with human subjects or with non-human subjects.

As shown in FIG. 1, system 10 includes medical device programmer 30, implantable medical device (IMD) 20, and lead 50. Lead 50 includes plurality of electrodes 60, and plurality of orientation markers 82 adjacent a distal end 54 of lead 50. IMD 20 includes a stimulation therapy module that includes an electrical stimulation generator that generates and delivers electrical stimulation therapy to one or more regions of brain 49 of patient 40 via one or more of electrodes 60. In the example shown in FIG. 1, system 10 may be referred to as a DBS system because IMD 20 provides electrical stimulation therapy directly to tissue within brain 49, e.g., a tissue site under the dura mater of brain 49. In other examples, one or more of lead 50 may be positioned to deliver therapy to a surface of brain 49 (e.g., the cortical surface of brain 49).

Lead 50 includes distal end 54 and a proximal end 52. As lead 50 is assembled, respective electrical connection sleeves (not shown in FIG. 1) adjacent proximal end 52 provide an electrical connection between IMD 20 and the conductive pathways of lead 50 running to electrodes 60 adjacent distal end 54 defined by the plurality of conductors of lead 50. Using the conductive pathways, IMD 20 may deliver electrical stimulation to patient 40 and/or sense electric signals of patient 40 using lead 50. While FIG. 1 illustrates proximal end of lead 50 connected directly to the header of IMD 20, in other examples, the proximal end of lead 50 may be connected to one or more lead extensions which are connected to the header of IMD 20 to electrically connect lead 50 to IMD 20.

In the example shown in FIG. 1, IMD 20 may be implanted within a subcutaneous pocket below the clavicle of patient 40. In other examples, IMD 20 may be implanted within other regions of patient 40, such as a subcutaneous pocket in the abdomen or buttocks of patient 40 or proximate the cranium 48 of patient 40. Proximal end 52 of lead 50 is coupled to IMD 20 via a connection sleeve block (also referred to as a header), which may include, for example, electrical contacts that electrically couple to respective electrical contacts at proximal end 52 of lead 50. The electrical contacts electrically couple the electrodes 60 carried by distal end 54 of lead 50. Lead 50 traverses from the implant site of IMD 20 within a chest cavity of patient 40, along the neck of patient 40 and through the cranium of patient 40 to access brain 49. Generally, IMD 20 is constructed of a biocompatible material that resists corrosion and degradation from bodily fluids. IMD 20 may comprise a hermetic housing to substantially enclose components, such as a processor, therapy module, and memory.

Lead 50 may be positioned to deliver electrical stimulation to one or more target tissue sites within brain 49 to manage patient symptoms associated with a disorder of patient 40. Lead 50 may be implanted to position electrodes 60 at desired locations of brain 49 through respective holes in cranium 48. Lead 50 may be placed at any location within brain 49 such that electrodes 60 are capable of providing electrical stimulation to target tissue sites within brain 49 during treatment. Although FIG. 1 illustrates system 10 as including a single lead 50 coupled to IMD 20, in some examples, system 10 may include more than one lead.

Lead 50 may deliver electrical stimulation via electrodes 60 to treat any number of neurological disorders or diseases in addition to movement disorders, such as seizure disorders or psychiatric disorders. Lead 50 may be implanted within a desired location of brain 49 via any suitable technique, such as through respective burr holes in a skull of patient 40 or through a common burr hole in the cranium 48. Lead 50 may be placed at any location within brain 49 such that electrodes 60 of lead 50 are capable of providing electrical stimulation to targeted tissue during treatment. In the examples shown in FIG. 1, electrodes 60 of lead 50 are shown as segmented electrodes and ring electrodes. Electrodes 60 of lead 50 may have a complex electrode array geometry that is capable of producing shaped electrical fields. In this manner, electrical stimulation may be directed to a specific direction from lead 50 to enhance therapy efficacy and reduce possible adverse side effects from stimulating a large volume of tissue.

IMD 20 may deliver electrical stimulation therapy to brain 49 of patient 40 according to one or more stimulation therapy programs. A therapy program may define one or more electrical stimulation parameter values for therapy generated and delivered from IMD 20 to brain 49 of patient 40. Where IMD 20 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 40, system 10 monitors electrical signals, such as, e.g., one or more bioelectrical brain signals of patient 40. For example, IMD 20 may include a sensing module that senses bioelectrical brain signals within one or more regions of brain 49. In the example shown in FIG. 1, the signals generated by electrodes 60 are conducted to the sensing module within IMD 20 via conductors within lead 50, including one or more conductors within lead 50 between distal end 54 and proximal end 52 of lead 50.

Programmer 30 wirelessly communicates with IMD 20 as needed to provide or retrieve therapy information. Programmer 30 is an external computing device that the user, e.g., the clinician and/or patient 40, may use to communicate with IMD 20. For example, programmer 30 may be a clinician programmer that the clinician uses to communicate with IMD 20 and program one or more therapy programs for IMD 20. Alternatively, programmer 30 may be a patient programmer that allows patient 40 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 20.

Programmer 30 may be a hand-held computing device with a display viewable by the user and an interface for providing input to programmer 30 (i.e., a user input mechanism). In other examples, programmer 30 may be a larger workstation or a separate application within another multi-function device, rather than a dedicated computing device. For example, the multi-function device may be a notebook computer, tablet computer, workstation, cellular phone, personal digital assistant, or another computing device that may run an application that enables the computing device to operate as a secure medical device programmer 30.

Again, while lead 50 is described here for use in DBS applications, lead 50 or other leads may be implanted at any other location within patient 40. For example, lead 50 may be implanted near the spinal cord, pudendal nerve, sacral nerve, cardiac tissue, or any other nerve or muscle tissue that may be the subject of stimulation or from which electrical signals are sensed via the electrodes. The user interface described herein may be used to program the stimulation parameters of any type of stimulation therapy. In the case of pelvic nerves, defining a stimulation field may allow the clinician to stimulate multiple desired nerves without placing multiple leads deep into patient 40 and adjacent to sensitive nerve tissue. Therapy may also be changed if leads migrate to new locations within the tissue or patient 40 no longer perceives therapeutic effects of the stimulation. The features or techniques of this disclosure may be useful in other types of medical applications.

As described herein, lead detection system 102 may receive imaging data from imaging device 100. In some examples, imaging device 100 may be a CT machine that generates CT imaging data that is received by lead detection system 102. Lead detection system may be any type of computing device that can analyze CT imaging data as described herein. In some examples, programmer 30, IMD 20, a remote server, or any other computing device may be configured to provide the functionality attributed to lead detection system 102 such as determining the orientation of lead 50 within patient 40. Lead detection system 102 may include processing circuitry configured to receive computed tomography (CT) image data representing lead 50 implanted within patient 40. The processing circuitry may identify, from the CT image data, at least one hypointensive portion and identify, from the CT image data, at least one hyperintensive portion. The processing circuitry may then determine, based on the at least one hypointensive portion and the at least one hyperintensive portion, an orientation of lead 50 within patient 40 and output the orientation of lead 50 with respect to at least one anatomical direction or anatomical structure of patient 40.

The hyperintensive portions and hypointensive portions may relate to relative intensity of the values of the CT imaging data. For example, the lead detection system 102 may apply one or more respective thresholds for determining which portions, pixels, or voxels of the CT imaging data are hyperintensive or hypointensive. In one example, lead detection system 102 identifies at least one hypointensive portion by determining voxels of the CT image data having an intensity below a hypointensive threshold. In some examples, the hypointensive threshold may be set to a value that is lower than an intensity value representative of soft tissue or other low intensity pixels or voxels that are representative of the patient. In this manner, any pixels or voxels below the hypointensive threshold may be determined as indicative of an artifact instead of any actual portion of the patient. Similarly, lead detection system 102 may identify at least one hyperintensive portion by determining voxels of the CT image data having an intensity exceeding a hyperintensive threshold. The hyperintensive threshold is different than the hypointensive threshold, such as the hyperintensive threshold having a value greater than the hypointensive threshold. For example, the hyperintensive threshold may be set to an intensity value just below intensity values representative of radiopaque metals or other materials that make up at least part of the radiopaque material of interest. In some examples, radiopaque tissues such as dense bone may be above the hyperintensive threshold. In other examples, the hyperintensive threshold may have an intensity value greater than bone but below the intensity value of radiopaque materials used on the radiopaque material of interest. In some examples, the intensity of any tissue of the patient (such as soft tissue or bone) falls between the hypointensive threshold and the hyperintensive threshold. In other examples, lead detection system 102 may determine hyperintensive and hypointensive portions may grouping similar pixel intensities, determining areas within a predetermined or relative range of intensities, or any other method of determining portions of the CT imaging data that are hyperintensive or hypointensive.

At least one hypointensive portion may be indicative of at least one orientation marker of the lead, such as one of the orientation markers 82. At least one hyperintensive portion may be representative of the lead, such as lead 50. In other examples, a hyperintensive portion may be representative of one of orientation markers 82, while one or more hypointensive portions may also be caused by the same one of orientation markers 82. In some examples, at least one of orientation markers 82 may be constructed with an asymmetrical shape, such as a shape that is asymmetrical with respect to the circumference of lead 50. In this manner, an orientation marker may only be located partially around the circumference of lead 50 or have a non-annular axial cross-section. In some examples, orientation markers 82 may have a generally triangular shape and disposed at different axial and perimeter locations on lead 50.

In one example, lead detection system 102 may be configured to identify the at least one hypointensive portion and the at least one hyperintensive portion from an axial slice of the CT image data corresponding to an axial location of at least one orientation marker 82 of lead 50. In some examples, two hypointensive portions may extend radially outward from a single hyperintensive portion. Lead detection system 102 may determine an axis through the at least one hypointensive portion and the at least one hyperintensive portion and determine the orientation of lead 50 based on a position of the axis with respect to the CT image data. In some examples, lead detection system 102 may identify at least one hypointensive portion by identifying a first hypointensive portion and a second hypointensive portion, where the hyperintensive is disposed between the first hypointensive portion and the second hypointensive portion. Lead detection system 102 may then determine, based on a position of the first hypointensive portion and the second hypointensive portion with respect to the hyperintensive portion, the orientation of lead 50.

In some examples, lead detection system 102 may determine the orientation of lead 50 within brain 49 by determining the orientation of two orientation markers 82 in different axial slices of the CT imaging data. For example, lead detection system 102 may identify, from a second axial slice of the CT image data different than a first axial slice, a second hypointensive portion and identify, from the second axial slice of the CT image data, a second hyperintensive portion. Lead detection system 102 may then determine a second axis through the second hypointensive portion and the second hyperintensive portion, wherein the first axis and the second axis have different orientations with respect to the lead. These different orientations with respect to the lead may be caused by different perimeter locations of orientation markers 82 on lead 40. Lead detection system 102 may then determine the orientation of lead 50, and the electrodes carried by the lead, based on a position of the first axis in the first axial slice relative to the position of the second axis in the second axial slice.

Although lead detection system 102 may determine the orientation of lead 50 based on CT imaging data corresponding to orientation markers, lead detection system 102 may confirm the lead orientation by identifying electrodes in the CT imaging data or independently determine the lead orientation by identifying hypointensive portions of the CT imaging data corresponding to electrodes carried by lead 50. For example, lead detection system 102 may be configured to identify each hypointensive portion of a plurality of hypointensive portions that extend away from the at least one hyperintensive portion in an axial slice of the CT image data. Lead detection system 102 may then determine a subset of hypointensive portions of the plurality of hypointensive portions that correspond to respective electrodes at different respective positions around a perimeter of the lead. Lead detection system 102 may determine the orientation of lead 50 based on locations of the subset of hypointensive portions. Lead detection system 102 may employ thresholding or other techniques for determining the subset of hypointensive portions. Although FIG. 1 illustrates a single lead 50, these techniques may be applied to determining the orientation of two or more leads implanted within patient 40. For example, respective leads may be implanted in the respective hemispheres of brain 49 for bilateral sensing and/or stimulation therapy.

Lead detection system 102 may include a display configured to output the determined orientation of lead 50 for presentation to a user. The display may present a representation of lead 50 and/or electrodes 60 with respect to an anatomical direction or anatomical structure of patient 40. In some examples, lead detection system 102 may control the display to present other information associated with lead implantation and/or orientation.

Figure 2:
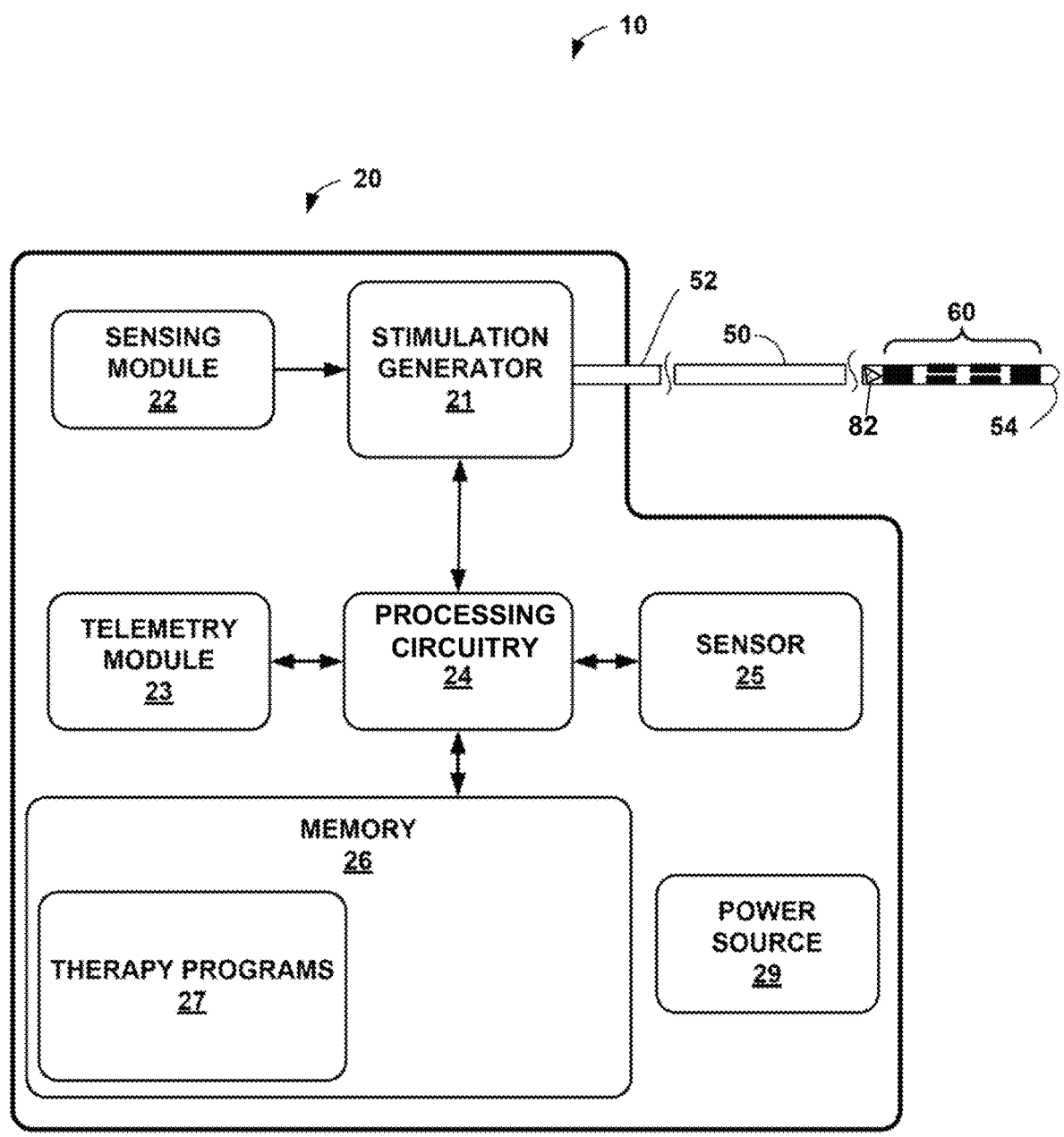
FIG. 2 is functional block diagram illustrating components of an example medical device.

FIG. 2 is a functional block diagram illustrating components of IMD 20. As shown, system 10 includes IMD 20 coupled to lead 50. In the example of FIG. 2, IMD 20 includes processor circuitry 24 (also referred to as "processor", "processors", or "processing circuitry"), memory 26, stimulation generator 21, sensing module 22, telemetry module 23, sensor 25, and power source 29. Each of these components (also referred to as "modules" may be or include electrical circuitry configured to perform the functions attributed to each respective module). For example, processor 24 may include processing circuitry, stimulation generator 21 may include switch circuitry, sensing module 22 may include sensing circuitry, and telemetry module 23 may include telemetry circuitry. Memory 26 may include any volatile or non-volatile media, such as a random-access memory (RAM), read only memory (ROM), non-volatile RAM (NVRAM), electrically erasable programmable ROM (EEPROM), flash memory, and the like. Memory 26 may store computer-readable instructions that, when executed by processor 24, cause IMD 20 to perform various functions. Memory 26 may be a storage device or other non-transitory medium.

Processor 24 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 24 herein may be embodied as firmware, hardware, software or any combination thereof.

Processor 24 controls stimulation generator 21 to apply particular stimulation parameter values, such as amplitude, pulse width, and pulse rate.

In the example shown in FIG. 2, lead 50 includes electrodes 60 located at distal end 54. Processor 24 also controls stimulation generator 21 to generate and apply the stimulation signals to selected combinations of electrodes of the electrode module. In some examples, stimulation generator 21 includes a switch module that couples stimulation signals to selected conductors within lead 50, which, in turn, delivers the stimulation signals across selected electrodes. Such a switch module may be a switch array, switch matrix, multiplexer, or any other type of switching module configured to selectively couple stimulation energy to selected electrodes and to selectively sense bioelectrical neural signals of the spine with selected electrodes.

In other examples, however, stimulation generator 21 does not include a switch module. In these examples, stimulation generator 21 comprises a plurality of pairs of voltage sources, current sources, voltage sinks, or current sinks connected to each of electrodes such that each pair of electrodes has a unique signal generator. In other words, in these examples, each of electrodes is independently controlled via its own signal generator (e.g., via a combination of a regulated voltage source and sink or regulated current source and sink), as opposed to switching signals between electrodes.

Stimulation generator 21 may be a single channel or multi-channel stimulation generator. In particular, stimulation generator 21 may be capable of delivering a single stimulation pulse or multiple stimulation pulses at a given time via a single electrode combination or multiple stimulation pulses at a given time via multiple electrode combinations. In some examples, however, stimulation generator 21 may be configured to deliver multiple channels on a time-interleaved basis. For example, a switch module of stimulation generator 21 may serve to time divide the output of stimulation generator 21 across different electrode combinations at different times to deliver multiple programs or channels of stimulation energy to patient 40. In another example, the stimulation generator 21 may control the independent sources or sinks on a time-interleaved bases.

Figure 3:
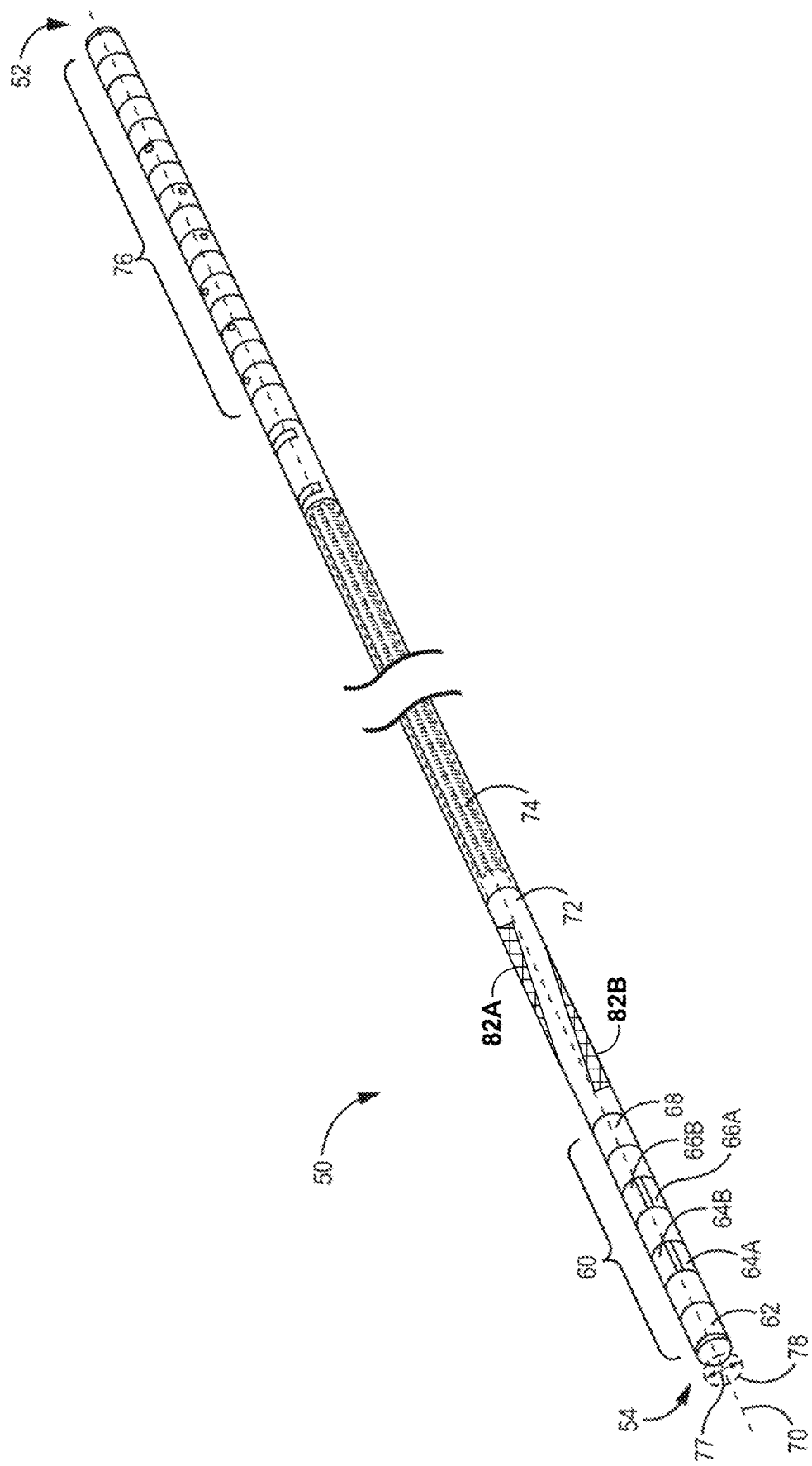
FIG. 3 is a conceptual diagram illustrating components of an example medical lead.

Lead 50 may include distal end 54 including a complex electrode array geometry (e.g., with one or more segmented electrodes along the longitudinal axis), but may also include one or more single ring electrodes along the longitudinal axis in other examples. It will be understood that "along the longitudinal axis" as used herein refers to an axial position along the length of the longitudinal axis that may be displaced radially from that axis. In one example, distal end 54 of lead 50 includes a plurality of electrodes 60 positioned at different axial positions along the longitudinal axis of the lead and a plurality of electrodes 60 positioned at different angular positions around the circumference of the lead/ around the longitudinal axis (which may be referred to as electrode segments). In this manner, electrodes may be selected along the longitudinal axis of lead 50 and along the circumference of the lead. Selectively activating electrodes 60 of lead 50 can produce customizable stimulation fields that may be directed to a particular side of lead 50 in order to isolate the stimulation field around the target anatomical region of brain 49. In the example of FIG. 3, lead 50 includes two ring electrodes 68, 62 with two segmented electrode rings 64, 66 each having three segmented electrodes (e.g., segmented electrodes 64A, 64B, 66A, 66B shown in FIG. 3) in between the respective electrodes 68, 62. The techniques described herein may be applied to leads having more or fewer segmented electrodes within a segmented electrode ring and/or to leads having more or fewer than two segmented electrode rings. These techniques may also be applied to leads having more or fewer than two ring electrodes. In yet other cases, lead 50 may include only segmented electrodes or only ring electrodes. In some examples, lead 50 may include a tip electrode which may be in the shape of a rounded cone or other shape that resides at the distal tip of lead 50.

Although sensing module 22 is incorporated into a common housing with stimulation generator 21 and processor 24 in FIG. 2, in other examples, sensing module 22 may be in a separate housing from IMD 20 and may communicate with processor 24 via wired or wireless communication techniques. Example bioelectrical signals include, but are not limited to, a signal generated from local field potentials within one or more regions of the spine or brain, for example.

Sensor 25 may include one or more sensing elements that sense values of a respective patient parameter. For example, sensor 25 may include one or more accelerometers, optical sensors, chemical sensors, temperature sensors, pressure sensors, or any other types of sensors. Sensor 25 may output patient parameter values that may be used as feedback to control delivery of therapy. IMD 20 may include additional sensors within the housing of IMD 20 and/or coupled as a separate module via one of lead 50 or other leads. In addition, IMD 20 may receive sensor signals wirelessly from remote sensors via telemetry module 23, for example. In some examples, one or more of these remote sensors may be external to patient (e.g., carried on the external surface of the skin, attached to clothing, or otherwise positioned external to the patient).

Telemetry module 23 supports wireless communication between IMD 20 and an external programmer (e.g., such as programmer 30) or another computing device under the control of processor 24. Processor 24 of IMD 20 may receive, as updates to programs, values for various stimulation parameters such as amplitude and electrode combination, from programmer 30 via telemetry module 23. The updates to the therapy programs may be stored within therapy programs 27 portion of memory 26. In some examples, IMD 20 may receive lead orientation information directly from lead detection system 102 or via programmer 30. Telemetry module 23 in IMD 20, as well as telemetry modules in other devices and systems described herein, such as programmer 30, may accomplish communication by radiofrequency (RF) communication techniques. In addition, telemetry module 23 may communicate with external medical device programmer 30 via proximal inductive interaction of IMD 20 with programmer 30. Accordingly, telemetry module 23 may send information to programmer 30 on a continuous basis, at periodic intervals, or upon request from IMD 20 or programmer 30.

Power source 29 delivers operating power to various components of IMD 20. Power source 29 may include a small rechargeable or non-rechargeable battery and a power generation circuit to produce the operating power. Recharging may be accomplished through proximal inductive interaction between an external charger and an inductive charging coil within IMD 20. In some examples, power requirements may be small enough to allow IMD 20 to utilize patient motion and implement a kinetic energy-scavenging device to trickle charge a rechargeable battery. In other examples, traditional batteries may be used for a limited period of time.

FIG. 3 is a conceptual diagram illustrating an example medical lead 50. In the example of FIG. 3, there are eight conductors corresponding to eight respective electrodes—2 ring electrodes and 6 segmented electrodes (two different axial locations with three electrodes around the perimeter at each axial location)—and eight electrical terminals, such that the lead 50 defines eight isolated electrical paths or channels for delivery of therapy and/or sensing of electrical signals by IMD 20. However, in other examples, greater or fewer conductors, electrodes, and terminals may be used. Lead 50 includes a distal end 54 and a proximal end 52, corresponding to an electrode end and a terminal end, respectively. Distal end 54 and proximal end 52 may define a longitudinal axis 70 along a length of lead 50. Lead 50 includes an outer perimeter 78 that has a diameter 77. In some examples, diameter 77 of outer perimeter 78 may be between approximately 25 millionth of an inch (mils) (0.635 millimeters (mm) and 100 mils (2.54 mm), although other values are contemplated.

Lead 50 may include a lead body 72 extending between distal end 54 and proximal end 52. Lead body 72 may be configured to provide structure and support to lead 50 and to encase at least a portion of a plurality of conductors 74. At least a portion of lead body 72 may include conductors in a coiled arrangement. In some examples, lead body 72 may act as an insulator between the plurality of conductors 74. In some examples, lead body 72 may extend through the length of lead 50 as a monolithic form. Lead body 72 may be formed from a polymeric material including, but not limited to, polyurethanes, silicones, fluoropolymers, fluoroelastomers, polyethylenes, polyesters, and other biocompatible polymers suitable for contact with bodily tissue.

Lead 50 may include a plurality of terminals 76 near proximal end 52. Each terminal of the plurality of terminals 76 may be configured to electrically couple to a conductor 74 within lead body 72 of lead 50 and a conductor external of lead 50, such as a contact of IMD 20 of FIG. 1. The plurality of terminals 76 may be positioned at or near proximal end 52 of lead 50. In some examples, each terminal in the plurality of terminals 76 may be a ring contact that extends around outer perimeter 78 of lead 50.

Lead 50 may include the plurality of electrical conductors 74 extending about longitudinal axis 70 of lead 50. The plurality of electrical conductors 74 may be electrically isolated from one another by lead body 72 to form separate channels, circuits, or conductive paths through the lead body 72 although techniques described herein also apply to lead body 72 carrying a single conductor. As shown in FIG. 3, the plurality of conductors 74 may be in a coiled arrangement for at least a portion of lead 50 (e.g., between the electrodes 60 and terminal terminals 76). The coiled arrangement of the plurality of conductors 74 may be wound around longitudinal axis 70 of lead 50. In some examples, the plurality of electrical conductors 74 may include an electrical insulator sheath around a conductive portion. The electrical insulator sheath may be configured to electrically insulate a conductor 74 from undesired contact with an electrode or terminal for which electrical contact is not intended for the conductor 74. In some examples, each of the plurality of electrical conductors 74 may have a diameter, with or without the electrical insulator sheath, between at least approximately 0.0025 in. (0.0635 mm) and approximately 0.0080 in. (0.2032 mm).

Each of the plurality of electrical conductors 74 may have a distal connection portion on a distal end and a proximal connection portion on a proximal end of each conductor. The distal and proximal connection portions may be configured to electrically couple each of the plurality of electrical conductors 74 to a respective electrode of the plurality of electrodes 60 and a respective terminal of the plurality of terminals 76. In some examples, the distal and proximal connection portions may include connections sleeves around a perimeter of the respective conductor, where a diameter of each connection sleeve may be larger, smaller, or the same size as a diameter of the remainder conductor body of the respective conductor. In some examples, such as for conductors having an electrical insulator sheath described above, the plurality of conductors 74 may not have distal or proximal connection portions that include connection sleeves. For example, a distal portion of the electrical insulator sheath of a conductor may be removed to expose a bare metal conductor. This bare metal conductor may operate as the distal connection portion to electrically contact an electrode or terminal. Each of the plurality of electrodes 60 may be formed from an electrically conductive material including, but not limited to, platinum, palladium, iridium, titanium and titanium alloys such as titanium molybdenum alloy (TiMoly), nickel and nickel alloys such as MP35N alloy, and the like. For example, electrodes may be formed from an 80/20 platinum/iridium alloy suitable for mechanical crimping.

Lead 50 may include a plurality of electrodes 60 near distal end 54. In the example of FIG. 3, the plurality of electrodes 60 includes ring electrodes 62 and 68, and segmented electrodes, such as segmented electrodes 64A, 64B, 66A, and 66B. While only segmented electrodes 64A, 64B, 66A, and 66B are shown, the segmented electrodes may form a discontinuous conductive ring that includes a plurality of electrodes, such as 64A, 64B, and an anterior electrode 64C (not shown) for an exemplary ring of three segmented electrodes on one ring (collectively referred to as "segmented electrode ring 64"), and 66A, 66B, and an anterior electrode 66C (not shown) on another ring (collectively referred to as "segmented electrode ring 66"). Each segmented electrode of a respective discontinuous segmented electrode ring is electrically isolated from the other segmented electrodes in the respective discontinuous segmented electrode ring. For example, segmented electrodes 64A and 64B, which are part of discontinuous segmented electrode ring 64, are electrically isolated from each other. In this example, there are two sets of three segmented electrodes forming segmented electrode rings 64 and 66 at distal end 54 of lead 50, such that each set of segmented electrodes forming segmented electrode rings 64 and 66 is aligned along a longitudinal axis of the electrode module and the sets are positioned circumferentially around outer perimeter 78 of lead 50. In other examples, one or more segmented electrodes may be positioned along the longitudinal axis without being symmetrically arranged around the longitudinal axis. For instance, a single segment spanning between 90 and 120 degrees may be the only electrode at a particular axial location along the length of the lead such that there is not radial symmetry.

The plurality of electrodes 60 of lead 50 may be constructed of a variety of different designs. For example, one or more leads 50 may include two or more electrodes at each longitudinal location along the length of the lead, such as multiple electrodes at different perimeter locations around outer perimeter 78 of lead 50 at each of the locations, such as by using electrode modules. As mentioned above, each electrode of the plurality of electrodes 60 may be electrically coupled to a respective electrical conductor of the plurality of electrical conductors 74. Each of the plurality of electrodes 60 may be formed from a biocompatible electrically conductive material including, but not limited to, platinum, palladium, iridium, and other biocompatible materials suitable for contact with bodily tissue. For example, electrodes may be formed from a 90/10 platinum/iridium alloy.

Referring to FIGS. 1-3, as discussed above, in some examples, it may be desirable for a clinician to be aware of the orientation and/or position of lead 50. For instance, it may be desirable for a clinician to be aware of the orientation and/or position of lead 50 when using programmer 30 to program IMD 20 to deliver electrical stimulation to patient 40 via electrodes 60 of lead 50.

In accordance with one or more techniques of this disclosure, system 10 may include lead detection system 102, which may be configured to determine an orientation and/or a location of lead 50 as implanted in patient 40. As shown in FIG. 1, lead detection system 102 may determine the orientation and/or the location of lead 50 based on image data captured by imaging device 100.

Imaging device 100 may represent any device capable of capturing images of a patient. Examples of imaging device 100 include, but are not necessarily limited to, x-ray imaging devices, computed tomography (CT) imaging devices, magnetic resonance imaging (MRI) devices, ultrasound imaging devices, and any other type of imaging device. In this manner, the image data from which hypointensive portions and/or hyperintensive portions are identified may be generated from different imaging modalities that may be imaging device 100. In one specific example imaging device 100 includes the O-Arm™ imaging system available from Medtronic Inc. In some examples, imaging device 100 may be capable of producing image data with a resolution at least (1.0 mm×1.0 mm×1.0 mm), (0.6 mm×0.6 mm×0.6 mm), (0.4 mm×0.4 mm×0.4 mm), . . . , (0.1 mm×0.1 mm×0.1 mm), or any other resolution suitable for imaging lead 50.

Imaging device 100 may provide image data corresponding to the captured image to other components of system 10, such as lead detection system 102. Imaging device 100 may provide the image data in any suitable format. Example formats include, but are not necessarily limited to, Analyze, Neuroimaging Informatics Technology Initiative (Nifti), Minc, and Digital Imaging and Communications in Medicine (DICOM).

Lead detection system 102 may represent a system configured to analyze image data to determine an orientation and/or a location of a lead implanted in a patient. In the example of FIG. 1, lead detection system 102 may analyze image data generated by imaging device 100 to determine an orientation and/or a location of lead 50 after lead 50 has been implanted in patient 40.

Lead 50 may include various features to facilitate lead detection system 102 in determining the orientation and/or the location. For instance, as shown in the example of FIG. 3, lead 50 may include orientation markers 82A and 82B (collectively, "orientation markers 82"). Orientation markers 82 may be located at specific positions within lead 50 relative to positions of electrodes 60 such that the rotational orientation of orientation markers 82 is a function of the rotational orientation of electrodes 60. Additionally, in some examples, orientation makers 82 may be positioned at a specific distance, or distances, along longitudinal axis 70 from one or more of electrodes 60. For instance, orientation makers 82 may be positioned at a specific distance along longitudinal axis 70 from the most distal electrode (i.e., electrode 62 in FIG. 3). Orientation markers 82 may also be disposed at respective different positions around the perimeter of lead 50.

In some examples, orientation markers 82 may be positioned at different positions along longitudinal axis 70. For instance, as shown in FIG. 3, orientation marker 82A may be positioned closer to a tip of distal end 54 than orientation marker 82B. As such, in some examples, orientation marker 82A may be referred to as an upper orientation marker and orientation marker 82B may be referred to as a bottom or lower orientation marker. As described below, positioning orientation markers 82 at different positions along longitudinal axis 70 enables lead detection system 102 to determine a specific rotational orientation of lead 50 (i.e., as opposed to determining two possible rotational orientations that are 180 degrees apart).

Orientation markers 82 may be formed from a material visible in images captured by imaging device 100. For instance, orientation markers 82 may be formed to include a radiopaque material such as at least one of barium sulfate, bismuth compounds, or tungsten. Orientation markers 82 may be formed in shapes to enable determination of the rotational orientation of lead 50. Example shapes include, but are not necessarily limited to, triangles, rectangles with windows, partial rings (e.g., a cross-section similar to a "C"), or the like.

Figures 4A, 4B:
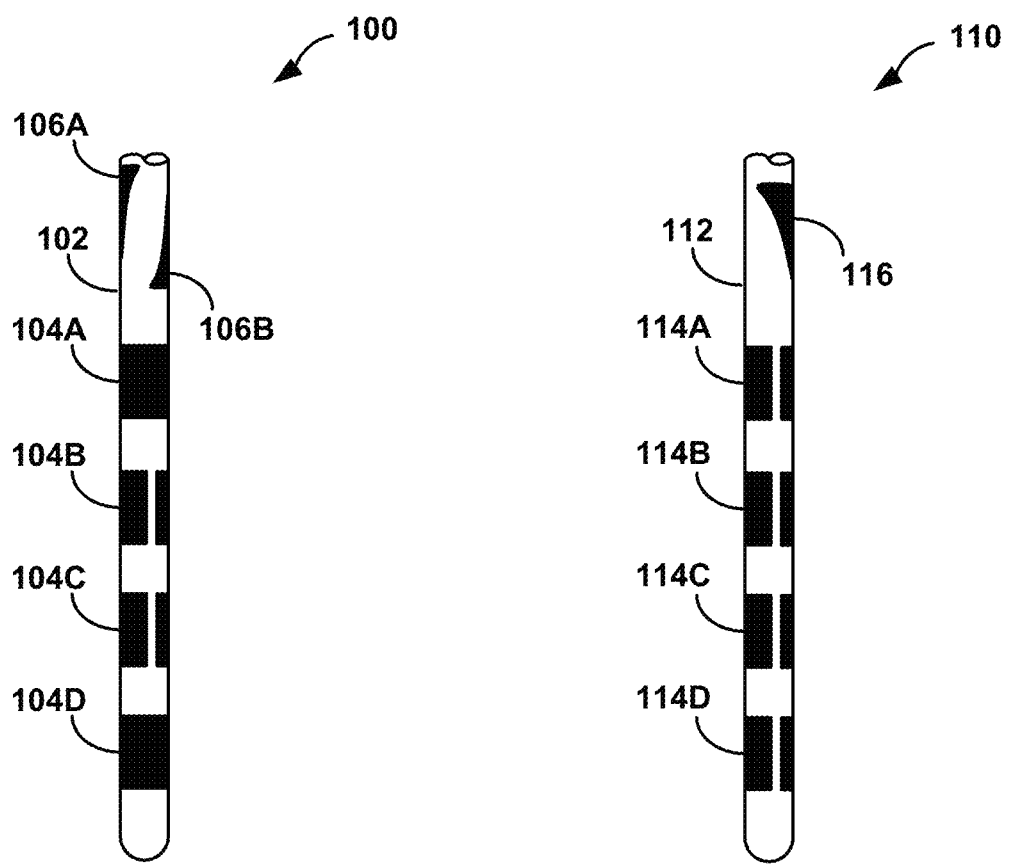
FIGS. 4A and 4B are conceptual diagrams of example leads with respective electrodes carried by the lead.

FIGS. 4A and 4B are conceptual diagrams of example leads 100 and 110, respectively, with respective electrodes carried by the lead. As shown in FIGS. 4A and 4B, leads 100 and 110 are examples of lead 50 shown in FIG. 1. As shown in FIG. 2A, lead 100 includes four electrode levels 104 (includes levels 104A-104D) mounted at various lengths of lead housing 102. Lead 100 is inserted into through cranium 48 to a target position within brain 49.

Lead 100 is implanted within brain 49 at a location determined by the clinician to be near an anatomical region to be stimulated. Electrode levels 104A, 104B, 104C, and 104D are equally spaced along the axial length of lead housing 102 at different axial positions. Each electrode level 104 may have one, two, three, or more electrodes located at different angular positions around the circumference (e.g., around the perimeter) of lead housing 102. As shown in FIG. 4A, electrode level 104A and 104D include a single respective ring electrode, and electrode levels 104B and 104C each include three electrodes at different circumferential positions. This electrode pattern may be referred to as a 1-3-3-1 lead in reference to the number of electrodes from the proximal end to the distal end of lead 100. Electrodes of one circumferential location may be lined up on an axis parallel to the longitudinal axis of lead 100. Alternatively, electrodes of different electrode levels may be staggered around the circumference of lead housing 102. In addition, lead 100 or 110 may include asymmetrical electrode locations around the circumference, or perimeter, of each lead or electrodes of the same level that have different sizes. These electrodes may include semi-circular electrodes that may or may not be circumferentially aligned between electrode levels.

Lead housing 102 may include orientation markers 106A and 106B, which are examples of orientation markers 82. The orientation markers 106A and 106B correspond to a certain circumferential location that allows lead 100 to the imaged when implanted in patient 112. Using the images of patient 40, the clinician can use the orientation markers 106A and 106B as a marker for the exact orientation of lead 100 within the brain 49 of patient 40 as described herein. Orientation of lead 100 may be used to easily program the stimulation parameters by generating the correct electrode configuration to match the stimulation field defined by the clinician. In other embodiments, a marking mechanism other than orientation markers 106A and 106B may be used to identify the orientation of lead 100. These marking mechanisms may include something similar to a tab, detent, or other structure on the outside of lead housing 102 or embedded within lead housing 102. In some embodiments, the clinician may note the position of markings along a lead wire during implantation to determine the orientation of lead 100 within patient 112.

FIG. 4B illustrates lead 110 that includes multiple electrodes at different respective circumferential positions at each of levels 114A-114D. Similar to lead 100, lead 110 is inserted through a burr hole in cranium 48 to a target location within brain 49. Lead 110 includes lead housing 112. Four electrode levels 114 (114A-114D) are located at the distal end of lead 110. Each electrode level 114 is evenly spaced from the adjacent electrode level and includes two or more electrodes. In one embodiment, each electrode level 114 includes three, four, or more electrodes distributed around the circumference of lead housing 112. Therefore, lead 110 includes 114 electrodes in a preferred embodiment. Each electrode may be substantially rectangular in shape. Alternatively, the individual electrodes may have alternative shapes, e.g., circular, oval, triangular, rounded rectangles, or the like. Lead 110 may include orientation marker 116 similar to one of orientation markers 106A and 106B, which may be an example of orientation markers 82. Lead 110 is an example of a lead that includes only one orientation marker.

In alternative embodiments, electrode levels 104 or 114 are not evenly spaced along the longitudinal axis of the respective leads 100 and 110. For example, electrode levels 104C and 104D may be spaced approximately 3 millimeters (mm) apart while electrodes 104A and 104B are 10 mm apart. Variable spaced electrode levels may be useful in reaching target anatomical regions deep within brain 49 while avoiding potentially undesirable anatomical regions. Further, the electrodes in adjacent levels need not be aligned in the direction as the longitudinal axis of the lead, and instead may be oriented diagonally with respect to the longitudinal axis.

Leads 100 and 110 are substantially rigid to prevent the implanted lead from varying from the expected lead shape. Leads 100 or 110 may be substantially cylindrical in shape. In other embodiments, leads 100 or 110 may be shaped differently than a cylinder. For example, the leads may include one or more curves to reach target anatomical regions of brain 49. In some embodiments, leads 100 or 110 may be similar to a flat paddle lead or a conformable lead shaped for patient 12. Also, in other embodiments, leads 100 and 110 may any of a variety of different polygonal cross sections (e.g., triangle, square, rectangle, octagonal, etc.) taken transverse to the longitudinal axis of the lead.

As shown in the example of lead 100, the plurality of electrodes of lead 100 includes a first set of three electrodes disposed at different respective positions around the longitudinal axis of the lead and at a first longitudinal position along the lead (e.g., electrode level 104B), a second set of three electrodes disposed at a second longitudinal position along the lead different than the first longitudinal position (e.g., electrode level 104C), and at least one ring electrode disposed at a third longitudinal position along the lead different than the first longitudinal position and the second longitudinal position (e.g., electrode level 104A and/or electrode level 104D). In some examples, electrode level 104D may be a bullet tip or cone shaped electrode that covers the distal end of lead 102.

Orientation markers 106A, 106B, or 116 are generally shown as triangular in shape with a curve that matches the curvature of the outside of the lead. However, shapes other than triangles are also contemplated. For example, shapes such as squares, rectangles, oblique angled shapes, or other shapes at any orientation with respect to the lead may enable hypointensive and/or hyperintensive portions of imaging data that can be employed to determine the orientation of the lead. In another example, an orientation marker may include a full circumferential portion and a partial circumferential portion such that the orientation is at least partially asymmetrical with respect to the cross-section of the lead. In some examples, multiple orientation markers may be disposed at different asymmetrical positions around the perimeter of the lead.

Figure 5A:
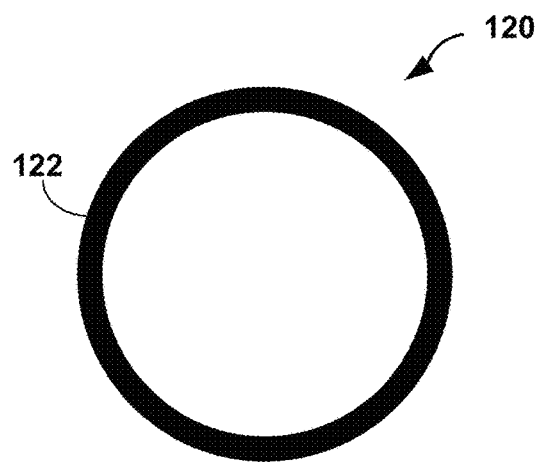
FIGS. 5A, 5B, 5C, and 5D are conceptual diagrams of example electrodes disposed around a perimeter of a lead at a particular longitudinal location.

FIGS. 5A-5D are transverse cross-sections of example stimulation leads having one or more electrodes around the circumference of the lead. As shown in FIGS. 5A-5D, one electrode level, such as one of electrode levels 104 and 114 of leads 100 and 110, are illustrated to show electrode placement around the perimeter, or around the longitudinal axis, of the lead. FIG. 5A shows electrode level 120 that includes circumferential electrode 122. Circumferential electrode 122 encircles the entire circumference of electrode level 120 and may be referred to as a ring electrode in some examples. Circumferential electrode 122 may be utilized as a cathode or anode as configured by the user interface.

Figure 5B:
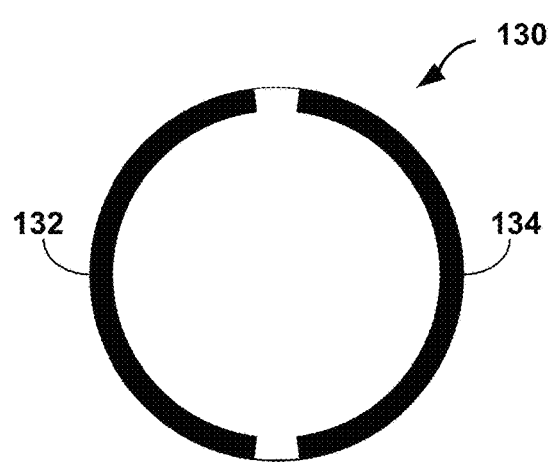

FIG. 5B shows electrode level 130 which includes two electrodes 132 and 134. Each electrode 132 and 134 wraps approximately 170 degrees around the circumference of electrode level 130. Spaces of approximately 10 degrees are located between electrodes 132 and 134 to prevent inadvertent coupling of electrical current between the electrodes. Smaller or larger spaces between electrodes (e.g., between 10 degrees and 30 degrees) may be provided in other examples. Each electrode 132 and 134 may be programmed to act as an anode or cathode.

Figure 5C:
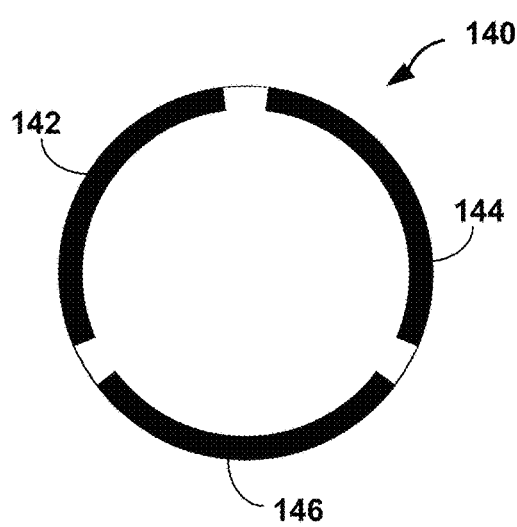

FIG. 5C shows electrode level 140 which includes three equally sized electrodes 142, 144 and 146. Each electrode 142, 144 and 146 encompass approximately 110 degrees of the circumference of electrode level 140. Similar to electrode level 130, spaces of approximately 10 degrees separate electrodes 142, 144 and 146. Smaller or larger spaces between electrodes (e.g., between 10 degrees and 30 degrees) may be provided in other examples. Electrodes 142, 144 and 146 may be independently programmed as an anode or cathode for stimulation.

Figure 5D:
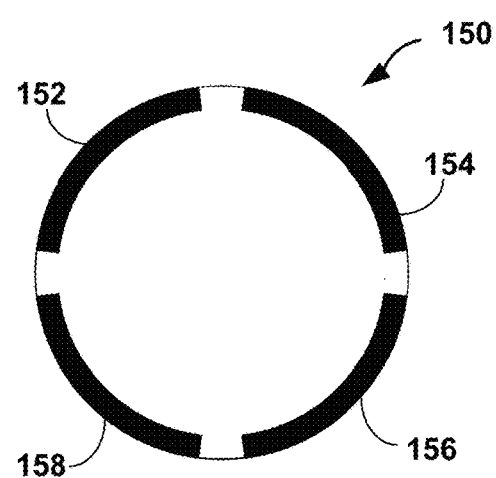

FIG. 5D shows electrode level 150 which includes four electrodes 152, 154, 156 and 158. Each electrode 152, 154, 156 and 158 covers approximately 80 degrees of the circumference with approximately 10 degrees of insulation space between adjacent electrodes. Smaller or larger spaces between electrodes (e.g., between 10 degrees and 30 degrees) may be provided in other examples. In other embodiments, up to ten or more electrodes may be included within an electrode level. In alternative embodiments, consecutive electrode levels of lead 114 may include a variety of electrode levels 120, 130, 140, and 150. For example, lead 114 (or any other lead described herein) may include electrode levels that alternate between electrode levels 130 and 150 depicted in FIGS. 5B and 5D. In this manner, various stimulation field shapes may be produced within brain 49 of patient 40. Further the above-described sizes of electrodes within an electrode level are merely examples, and the invention is not limited to the example electrode sizes.

Also, the insulation space, or non-electrode surface area, may be of any size. Generally, the insulation space is between approximately 1 degree and approximately 20 degrees. More specifically, the insulation space may be between approximately 5 and approximately 15 degrees. In other examples, insulation space may be between approximately 10 degrees and 30 degrees or larger. Smaller insulation spaces may allow a greater volume of tissue to be stimulated. In alternative embodiments, electrode size may be varied around the circumference of an electrode level. In addition, insulation spaces may vary in size as well. Such asymmetrical electrode levels may be used in leads implanted at tissues needing certain shaped stimulation fields.

Figure 6:
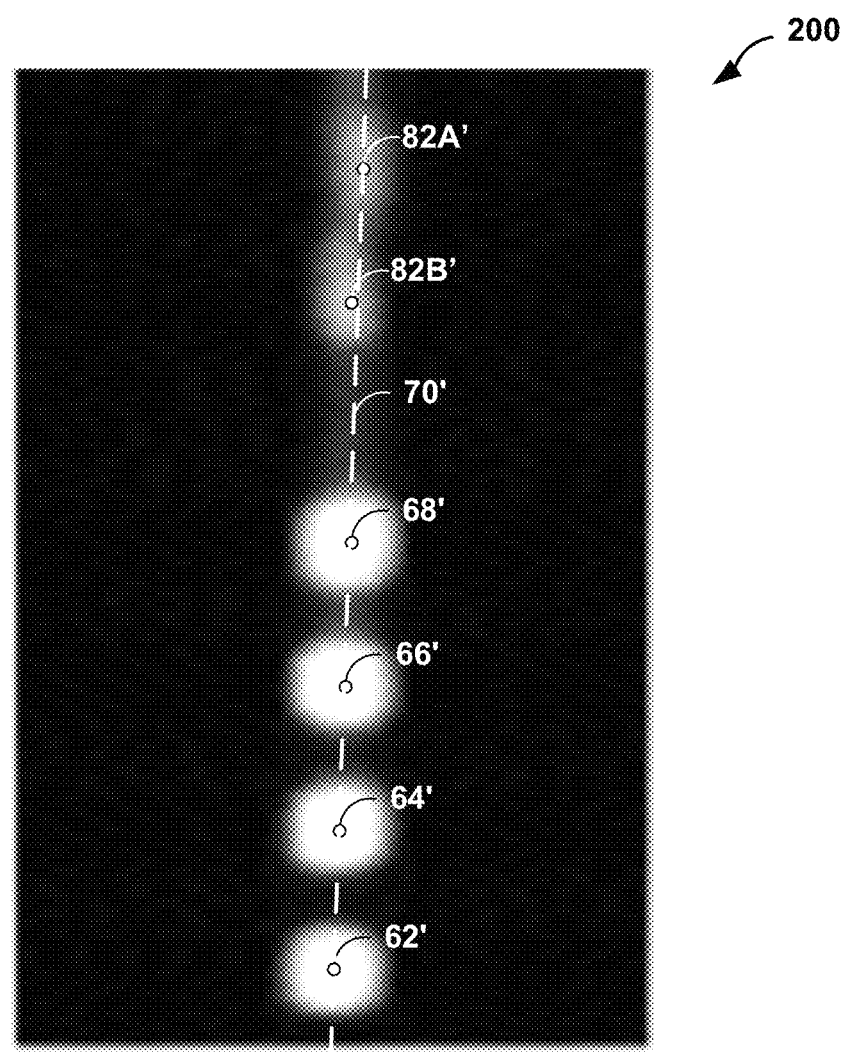
FIG. 6 is an example image generated by an imaging device of an implanted lead in a patient, in accordance with one or more techniques of this disclosure.

FIG. 6 is an example image generated by an imaging device of an implanted lead in a patient. In the example of FIG. 6, lead detection system 102 may receive (e.g., from imaging device 100) image data that represents an image of patient 40 after lead 50 has been implanted in patient 40. FIG. 4 is an example of an image generated by imaging device 100 that includes lead 50, or at least visible components of lead 50, in accordance with one or more techniques of this disclosure. As shown in FIG. 6, image 200 may correspond to an image of lead 50 of FIG. 3 implanted in patient 40, and image 200 may illustrate the longitudinal length of lead 50.

Lead detection system 102 may analyze the image data to determine the orientation and/or position of lead 50. For instance, lead detection system 102 may identify respective locations (e.g., centroids) of electrodes 60 and respective locations of orientation markers 82. As shown in FIG. 6, lead detection system 102 may identify centroid 82A' of orientation marker 82A, centroid 82B' of orientation marker 82B, centroid 62' of electrode 62, centroid 64' of electrode 64, centroid 66' of electrode 66, and centroid 68' of electrode 68 (segmented electrodes 64A and 64B are aggregated into a single electrode in image 200 having centroid 64', and segmented electrodes 66A and 66B are aggregated into a single electrode in image 200 having centroid 66'). The lighter portions of image 200 may correspond to higher intensities of CT image data. However, noise present in image 200 may limit the ability of lead detection system 102 to identify the orientation of lead 50 according to centroids 82A' and 82B'. As described below, lead detection system 102 may determine the lead orientation based on low intensity, or hypointensive portions, present in CT imaging data to improve orientation detection accuracy.

Figure 7B:
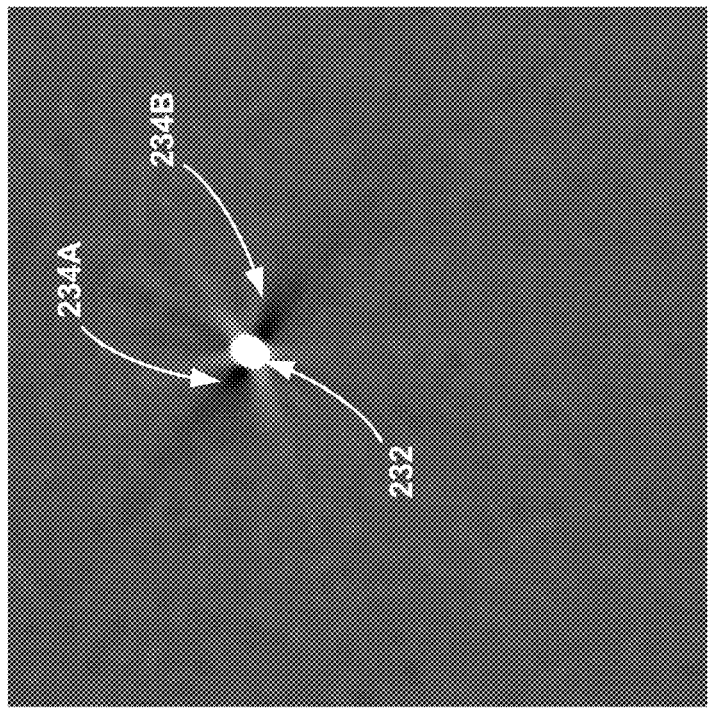
FIGS. 7A and 7B are example CT images of different axial slices of a lead including hypotensive and hypertensive portions.
Figure 7A:
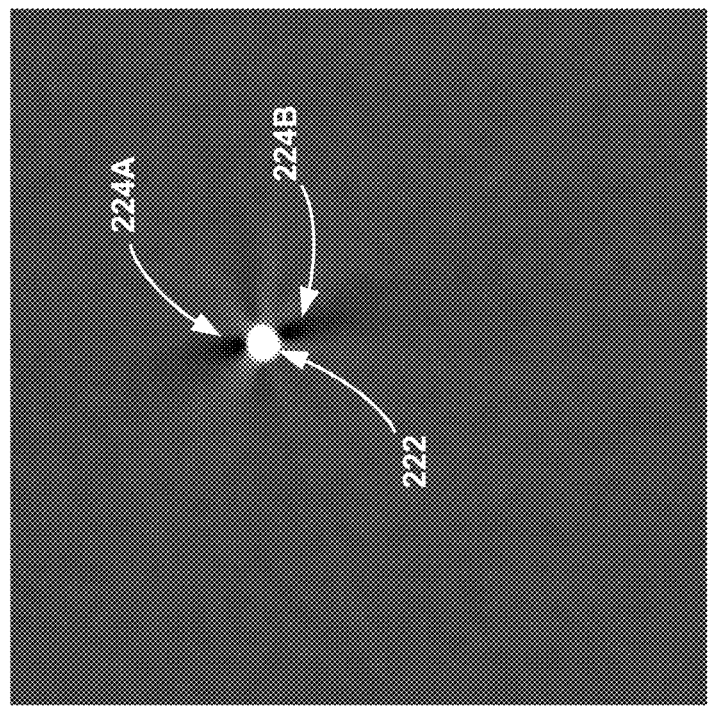

FIGS. 7A and 7B are example CT images of different axial slices 220 and 230 of a lead including hypotensive and hypertensive portions. White areas within axial slices 220 and 230 include high intensity values (e.g., hyperintensive portions) and dark areas within axial slices 220 and 230 include low intensity values (e.g., hypointensive portions). The remaining grey areas are generally reflective of soft tissue (e.g., brain tissue). Axial slices 220 and 230 are referred to as axial slices because they depict the axial view of the lead in which the lead would be positioned as running into and out of slice 220 and 230.

As shown in FIG. 7A, axial slice 220 is a two dimensional (2D) slice of CT imaging data received by lead detection system 102. Hyperintensive portion 222 is indicative of the orientation marker at this axial location (e.g., orientation marker 82A) which is located on the body of lead 50. Axial slice 220 also include hypointensive portions 224A and 224B. Hypointensive portion 224A extends in a radial direction away from hyperintensive portion 222, and hypointensive portion 224B extends in an opposing radial direction away from hyperintensive portion 222. Hypointensive portions 224A and 224B are not indicative of artificial or anatomical structures within the patient. Instead, the shape of orientation marker 82A may cause the CT imaging data to include hypointensive portions 224A and 224B. In this manner, hypointensive portions 224A and 224B may be referred to as artifacts in the CT imaging data caused by the orientation of orientation marker 82A of lead 50.

Similar to FIG. 7A, FIG. 7B illustrates axial slice 230 that is a two dimensional (2D) slice of CT imaging data received by lead detection system 102. Hyperintensive portion 232 is indicative of the orientation marker at this axial location (e.g., orientation markers 82B) which is located on at a different axial location along the body of lead 50 than orientation marker 82A. Axial slice 230 also include hypointensive portions 234A and 234B. Hypointensive portion 234A extends in a radial direction away from hyperintensive portion 232, and hypointensive portion 234B extends in an opposing radial direction away from hyperintensive portion 232. Hypointensive portions 234A and 234B are not indicative of artificial or anatomical structures within the patient. Instead, the shape of orientation marker 82B may cause the CT imaging data to include hypointensive portions 234A and 234B. In this manner, hypointensive portions 234A and 234B may be referred to as artifacts in the CT imaging data caused by the orientation of orientation marker 82B of lead 50.

Orientation markers 82A and 82B are disposed at different circumferential locations around the perimeter of lead 50. Therefore, hypointensive portions 224A and 224B of axial slice 220 extend away from hyperintensive portion 222 at different circumferential locations than the locations at which hypointensive portions 234A and 234B extend away from hyperintensive portion 232 of axial slice 230.

FIGS. 8A and 8B are example thresholded representations of the hypotensive and hypertensive portions of the CT images of axial slices 220 and 230 of FIGS. 7A and 7B, respectively. In order to identify hyperintensive portions and hypointensive portions from CT image data, lead detection system 102 may use a technique such as thresholding the pixels or voxels of the CT image data. For example, lead detection system 102 may apply a hypointensive threshold to the CT image data and determine any voxels below the hypointensive threshold as being included in a hypointensive portions. Conversely, lead detection system 102 may apply a hyperintensive threshold to the CT image data and determine any voxels exceeding the hyperintensive threshold as being included in a hyperintensive portion. Lead detection system 102 may then analyze the resulting hyperintensive and hypointensive portions to determine the orientation of the lead.

As shown in FIG. 8A, axial slice 320 may be the result of lead detection system 102 applying thresholds to the CT image data of axial slice 220. Axial slice 320 may thus include hyperintensive portion 322 (which corresponds to hyperintensive portion 222 of FIG. 7A) and hypointensive portions 324A and 324B (which correspond to hypointensive portions 224A and 224B, respectively). Lead detection system 102 may then determine axis 326 that bisects hypointensive portions 324A and 324B. In some examples, lead detection system 102 may require that axis 326 runs through at least a portion of hyperintensive portion 322 which is indicative of the location of lead 50. In other examples, lead detection system 102 may determine axis 326 without the need for hyperintensive portion 322.

Although axis 326 may indicate a general orientation of orientation marker 82A, for example, axis 326 may only provide two options for the location of orientation marker 82A. In other words, orientation marker 82A may be positioned perpendicular to axis 326, and axis 326 may only indicate two possible locations of ordinary marker 82A, such on either side of axis 326. In this situation, lead detection system 102 may determine the orientation of lead 50 based on axis 326 of axial slice 320 and axis 336 of axial slice 330 as shown in FIG. 8B. In other examples, lead detection system 102 may analyze the spatial relationship of hyperintensive portion 322 with respect to axis 326 to determine the orientation of marker 82A. The larger area or volume of hyperintensive portion 322 on one side of axis 326 may be indicative of orientation marker 82A being located on that side of axis 326. In this manner, lead detection system 102 may determine the circumferential orientation of orientation marker 82A and lead 50 based on the spatial relationship of hyperintensive portion 322 with respect to hypointensive portions 324A and 324B.

As shown in FIG. 8B, axial slice 330 may be similar to axial slice 320 of FIG. 8A. Axial slice 330 may be the result of lead detection system 102 applying thresholds to the CT image data of axial slice 230. Axial slice 330 may thus include hyperintensive portion 332 (which corresponds to hyperintensive portion 232 of FIG. 7B) and hypointensive portions 334A and 334B (which correspond to hypointensive portions 234A and 234B, respectively). Lead detection system 102 may then determine axis 336 that bisects hypointensive portions 334A and 334B. In some examples, lead detection system 102 may require that axis 336 runs through at least a portion of hyperintensive portion 332 which is indicative of the location of lead 50. In other examples, lead detection system 102 may determine axis 336 without the need for hyperintensive portion 332. When lead detection system 102 employs axes 326 and 336, lead detection system 102 can determine the orientation of lead 50 because axes 326 and 336 are offset by the same known angle as orientation markers 82A and 82B, respectively. This offset may be less than 90 degrees to ensure that only a single circumferential orientation is possible when identifying the location of both orientation markers 82A and 82B.

In some examples, lead detection system 102 may be configured to identify the orientation of each lead, or each set of electrodes carried on a lead, independently with respect to surrounding tissue or other orientation of the patient. In other examples, lead detection system 102 may be configured to at least partially determine the orientation of multiple leads within the patient based on one or more hypointensive and hyperintensive portions associated with each lead and their spatial orientation with respect to each other. For example, lead detection system 102 may image two leads within a same field of view. Lead detection system 102 may be configured to identify the orientation of each lead with respect to each other based on the respective one or more hyperintensive and/or hypointensive portions from each lead. Since each lead may be implanted in known respective regions, such as one lead in each hemisphere, lead detection system 102 may determine that a line or plane between each lead corresponds to a coronal plane or other oblique plane based on implantation planning and/or implant records. Lead detection system 102 can then determine the rotational position of each lead with respect to the plane determined by the leads in the same field of view. In this manner, lead detection system 102 may be configured to utilize spatial orientation of two or more leads within the imaging data, in addition to the hypointensive and/or hyperintensive portions of the imaging data, to determine the orientation of each lead within the patient.

Figure 9B:
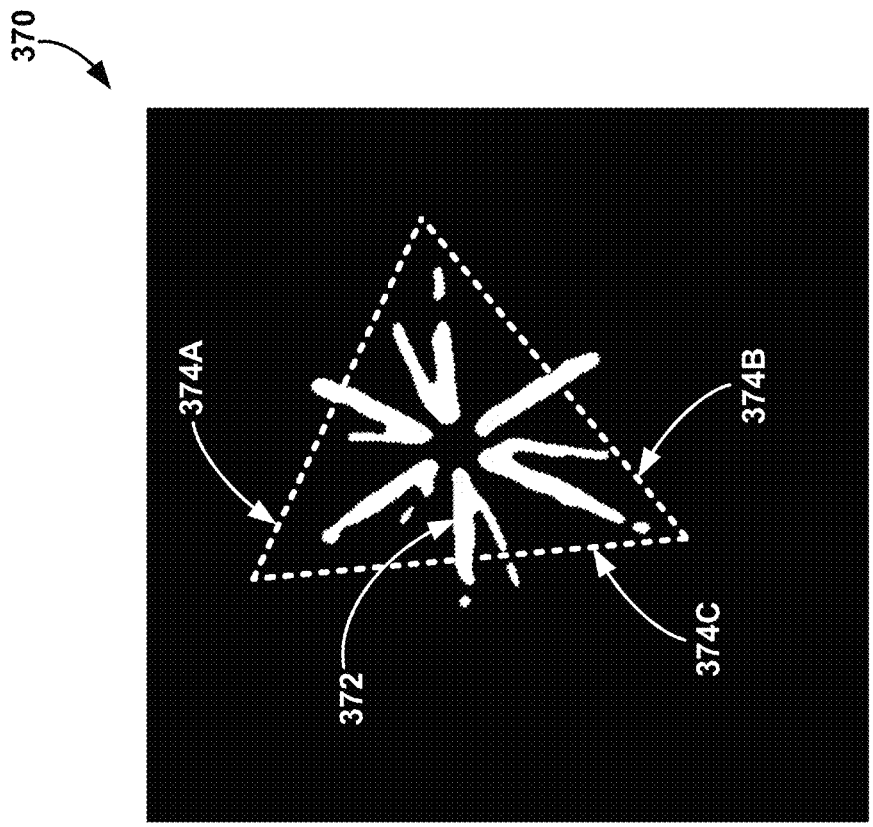
FIG. 9B is an example thresholded representation of the hypotensive and hypertensive portions of the CT image of FIG. 9A.
Figure 9A:
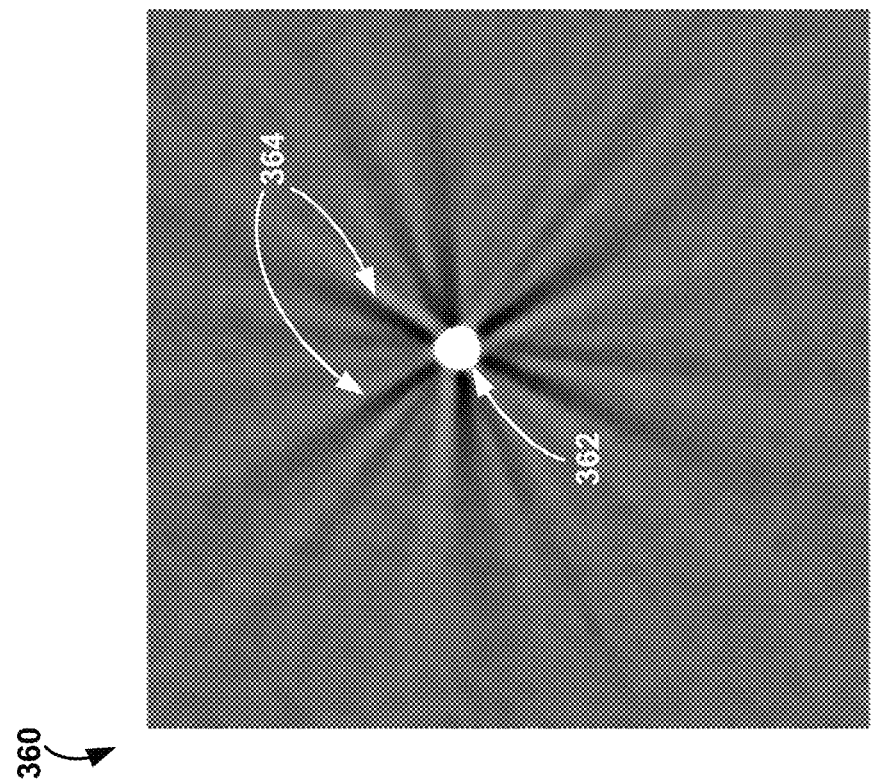
FIG. 9A is an example CT image of an axial slices of a lead including hypotensive and hypertensive portions at an axial position that includes multiple electrodes.

FIG. 9A is an example CT image of a axial slice of a lead including hypotensive and hypertensive portions at an axial position that includes multiple electrodes. Similar to FIGS. 7A and 7B, FIG. 9A includes white areas within axial slice 360 that includes high intensity values (e.g., hyperintensive portions) and dark areas within axial slice 360 include low intensity values (e.g., hypointensive portions). The remaining grey areas are generally representative of soft tissue (e.g., brain tissue) around the lead. Axial slice 360 may be referred to as an axial slice because it depicts the axial view of the lead in which the lead would be positioned as running into and out of slice 360.

As shown in FIG. 9A, axial slice 360 is a two dimensional (2D) slice of CT imaging data received by lead detection system 102. Hyperintensive portion 362 is indicative of the electrodes or other structures of lead 50 at this axial location (e.g., three electrodes 66 positioned around the perimeter of lead 50) which is located on the body of lead 50. Axial slice 360 also include hypointensive portions 364. Hypointensive portions 364 extend in a radial direction away from hyperintensive portion 362. Six large hypointensive portions 364 are shown as extending radially away from hyperintensive portion 362, but other smaller hypointensive portions can also be identified. Hypointensive portions 364 are not indicative of artificial or anatomical structures within the patient. Instead, the shape and position of electrodes around the perimeter of lead 50 may cause the CT imaging data to include hypointensive portions 364. In this manner, hypointensive portions 364 may be referred to as artifacts in the CT imaging data caused by the orientation of electrodes.

FIG. 9B is an example thresholded representation of the hypotensive and hypertensive portions 364 of the CT image slice 360 of FIG. 9A. As shown in FIG. 9B, lead detection system 102 may generate axial slice 370 by applying a hypointensive threshold to the CT image data of axial slice 360. In order to identify hyperintensive portions and hypointensive portions from CT image data, lead detection system 102 may use a technique such as thresholding the pixels or voxels of the CT image data. For example, lead detection system 102 may apply a hypointensive threshold to the CT image data and determine any voxels below the hypointensive threshold as being included in a hypointensive portions. Although not shown in the example of FIG. 9B, lead detection system 102 may apply a hyperintensive threshold to the CT image data and determine any voxels exceeding the hyperintensive threshold as being included in a hyperintensive portions. Lead detection system 102 may then analyze the resulting hyperintensive and/or hypointensive portions to determine the orientation of the electrodes and, by extension, the lead.

Axial slice 370 may thus include hypointensive portions 372 which correspond to hypointensive portions 364 of FIG. 9A. Although there are six larger hypointensive portions 372, three hypointensive portions may correspond to the center of a respective electrode and the other three hypointensive portions may correspond to the gap between adjacent electrodes. Lead detection system 102 may analyze hypointensive portions 372 for one or more characteristics that may be indicative of which hypointensive portions correspond to electrode locations and which hypointensive portions correspond to the gaps between the electrode locations. In one example, hypointensive portions having a relatively wider portion may correspond to the electrode locations. In addition, or alternatively, hypointensive portions extending longer from the center of hypointensive portions 372 may correspond to the gaps between electrodes. Lead detection system 102 may thus compare one or more characteristics of one or more hypointensive portions of hypointensive portions 372 and determine, based on the one or more characteristics, the position of each electrode at that axial location of axial slice 379. For example, dotted lines 374A, 374B, and 374C correspond to the generate surface direction of corresponding electrodes. Lead detection system 102 may utilize this electrode orientation to determine lead orientation and/or confirm the lead orientation determined from one or more orientation markers as described herein, such as in FIGS. 8A and/or 8B.

Figure 10:
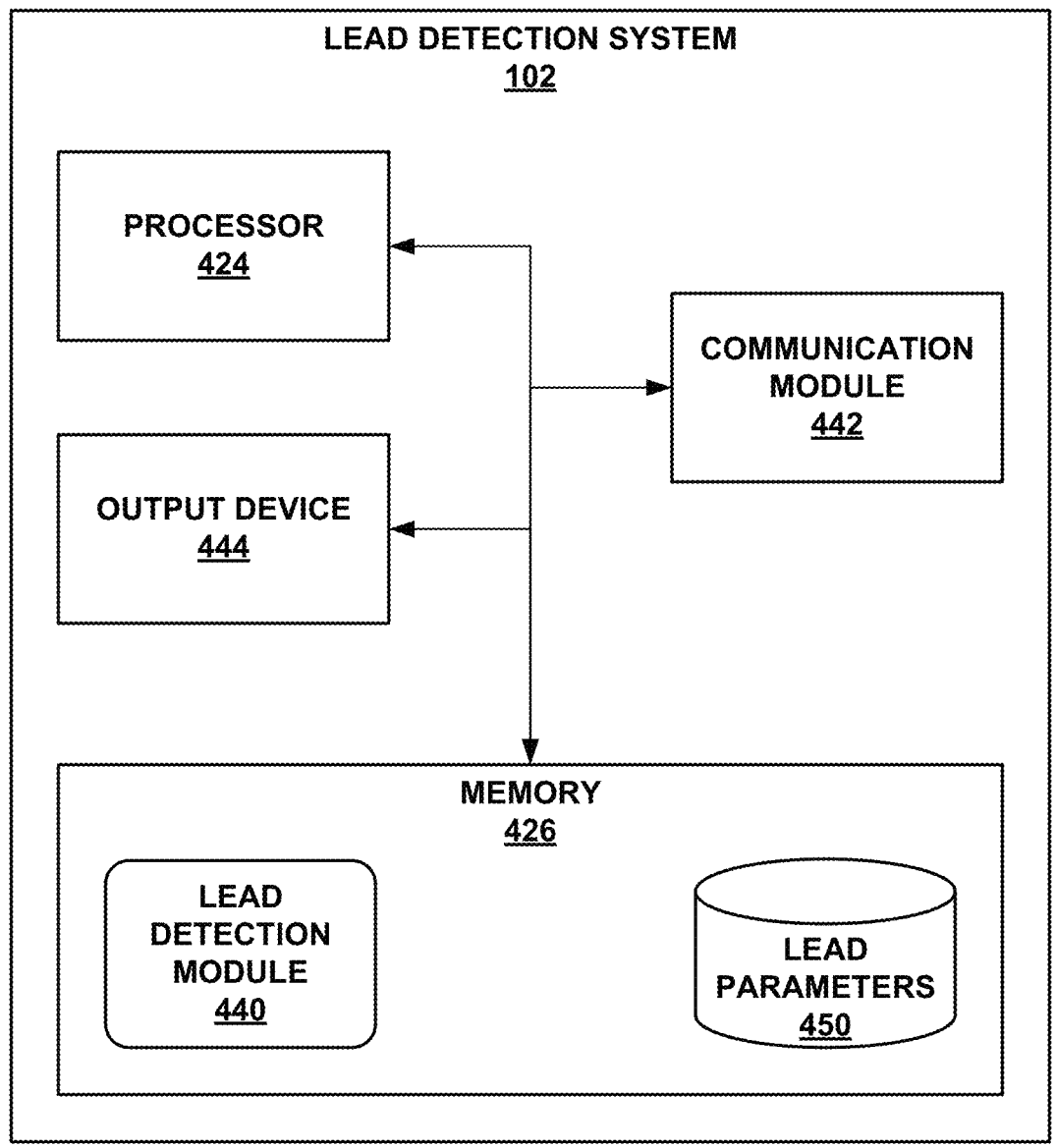
FIG. 10 is functional block diagram illustrating components of an example lead detection system.

FIG. 10 is a functional block diagram illustrating components of lead detection system 102. Examples of lead detection system 102 include, but are not necessarily limited to, desktops, tablets, laptops, mainframes, cloud computing environments, servers, or any type of other computing system. As one specific example, lead detection system 102 may be the StealthStation™ S8, available from Medtronic Inc. In the example of FIG. 10, lead detection system 102 includes processor circuitry 424 (also referred to as "processor"), memory 426, and communication module 428. Each of these components (also referred to as "modules" may be or include electrical circuitry configured to perform the functions attributed to each respective module).

Processor 424 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 424 herein may be embodied as firmware, hardware, software or any combination thereof.

Memory 426 may include any volatile or non-volatile media, such as a random-access memory (RAM), read only memory (ROM), non-volatile RAM (NVRAM), electrically erasable programmable ROM (EEPROM), flash memory, and the like. Memory 426 may store computer-readable instructions that, when executed by processor 424, cause lead detection system 102 to perform various functions. Memory 426 may be a storage device or other non-transitory medium. As shown in FIG. 10, memory 426 may store lead detection module 440 and lead parameters 450.

Lead parameters 450 may include various parameters about leads, such as lead 50. Examples of parameters that may be included in lead parameters 450 include, but are not limited to, such as models of leads (e.g., CAD models, template models, etc.), coordinates of centers of orientation markers and electrodes of the lead, distances between orientation markers and electrodes of the lead, angles between a vector connecting the orientation markers and centers of the electrodes, or any other parameters. In some examples, lead parameters 450 may include respective sets of lead parameters for different models of leads. For instance, lead parameters 450 may include a first set of lead parameters for a first lead model and a second set of lead parameters for a second lead model. Although not necessary to the lead orientation determination described herein, processor 424 may utilize one or more lead parameters to facilitate determination of which axial slices should correspond to orientation markers or electrodes, reduce possible locations of orientation markers or electrodes, or confirm the lead orientation based on hypointensive portions as described herein.

Communication module 442 may communicate with external devices via one or more wired and/or wireless networks by transmitting and/or receiving network signals on the one or more networks. Examples of communication module 442 include a network interface card (e.g. such as an Ethernet card), an optical transceiver, a radio frequency transceiver, a GPS receiver, or any other type of device that can send and/or receive information. Other examples of communication units 442 may include short wave radios, cellular data radios, wireless network radios, as well as universal serial bus (USB) controllers.

In accordance with one or more techniques of this disclosure, lead detection module 440 may be executable by processor 424 to determine a location and/or orientation of a lead implanted in a patient based on image data representing the lead implanted in the patient (e.g., image data generated by an imaging device, such as imaging device 100 of FIG. 1) as described herein. The image data may represent a relatively small volume of interest containing the lead (e.g., the portion of the lead carrying the electrodes and the orientation markers). In some examples, lead detection module 440 may perform pre-processing on the image data. For instance, lead detection module 440 may use linear interpolation to resample the volume of interest to a fixed voxel resolution (e.g., 0.1 mm×0.1 mm×0.1 mm).

Lead detection module 440 may determine various parameters of the lead. As one example, lead detection system 440 may receive a representation of user input indicating a manufacturer and model of the lead. As another example, lead detection system 440 may receive a message from the IMD indicating a manufacturer and model of the lead (e.g., via a telemetry link). Based on the manufacturer and model, lead detection module 440 may query lead parameters 450 to determine the parameters of the lead. Lead detection module 440 may perform the various techniques described herein for determining lead orientation based on imaging data and hypointensive portions identified within the imaging data.

Regardless of the particular technique utilized, lead detection module 440 may generate an output that includes any combination of the following: location of electrodes with respect to patient anatomical direction and/or anatomical structures, the centroid of distal electrode (3D point) in voxel coordinates, the direction of lead trajectory (from distal electrode towards proximal electrode (3D vector), the direction of the center of a target electrode segment (3D vector, perpendicular to the direction of the lead trajectory), a confidence score (e.g., a value representing the likelihood that the other outputs are accurate), or any other indication or representation of lead orientation and/or electrode position within patient 40.

Lead detection module 440 may provide the output via any channel. As one example, lead detection module 440 may cause output device 144 to display a graphical representation of the lead overlaid on an image of the patient in which the lead is implanted. The graphical representation may show the orientation and/or location of the lead relative to the patient (e.g., relative to one or more anatomical structures of the patient). As another example, lead detection module 440 may cause output device 144 to display numerical representations of any combination of the outputs described above.

Figure 11:
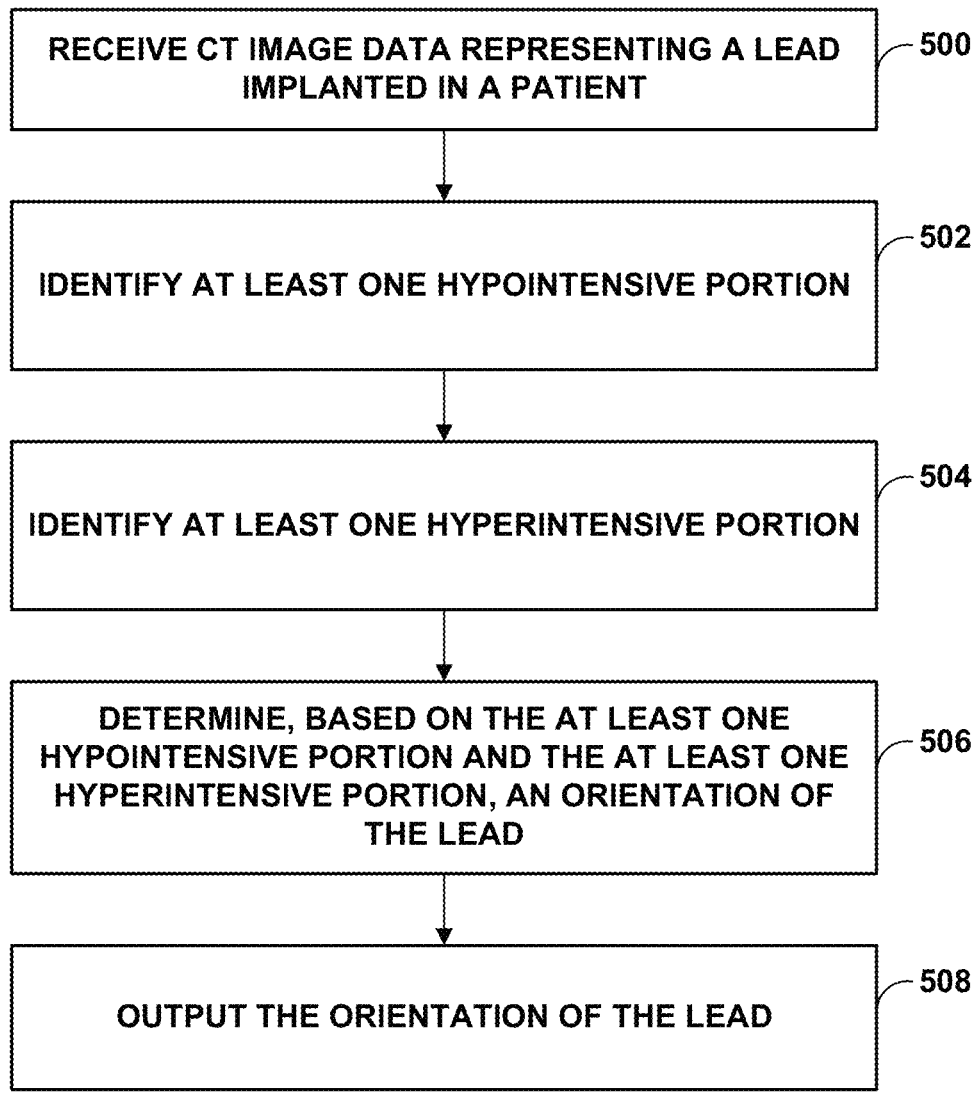
FIG. 11 is a flow diagram illustrating an example technique for determining the orientation of a lead implanted in a patient, in accordance with one or more techniques of this disclosure.

FIG. 11 is a flow diagram illustrating an example technique for determining the orientation of a lead implanted in a patient, in accordance with one or more techniques of this disclosure. For purposes of explanation, the technique of FIG. 11 will be described with respect to lead detection system 102 of FIGS. 1 and 10. However, lead detection systems other than lead detection system 102 may perform some or all of the technique of FIG. 11.

In the example of FIG. 11, lead detection system 102 receives or otherwise obtains CT image data representing a lead implanted in a patient (500). For instance, communication module 442 of lead detection system 102 may obtain, from imaging device 100, computed tomography (CT) images of patient 40 of FIG. 1 of a region of patient 40 in which lead 50 is implanted. As discussed above, example formats of the image data include, but are not necessarily limited to, Analyze, Neuroimaging Informatics Technology Initiative (Nifti), Minc, and Digital Imaging and Communications in Medicine (DICOM).

Lead detection system 102 then identifies at least one hypointensive portion within the axial slice of the CT image data (502). For example, lead detection system 102 may apply a hypointensive threshold to the CT image data to determine all voxels below the hypointensive threshold. Lead detection system 102 also identifies at least one hyperintensive portion within the axial slice of the CT image data (504). For example, lead detection system 102 may apply a hyperintensive threshold to the CT image data to determine all voxels exceeding the hyperintensive threshold. Lead detection system 102 then determines, based on the at least one hypointensive portion and the at least one hyperintensive portion, the orientation of lead 50 implanted within the patient (506). Lead detection system 102 also outputs the determined orientation of lead 50 (508). For example, lead detection system 102 may transmit the orientation to programmer 30 to facilitate stimulation parameter selection for therapy or output, for display, a graphical representation of the orientation of the lead, and electrodes, with respect to patient 40.

Figure 12:
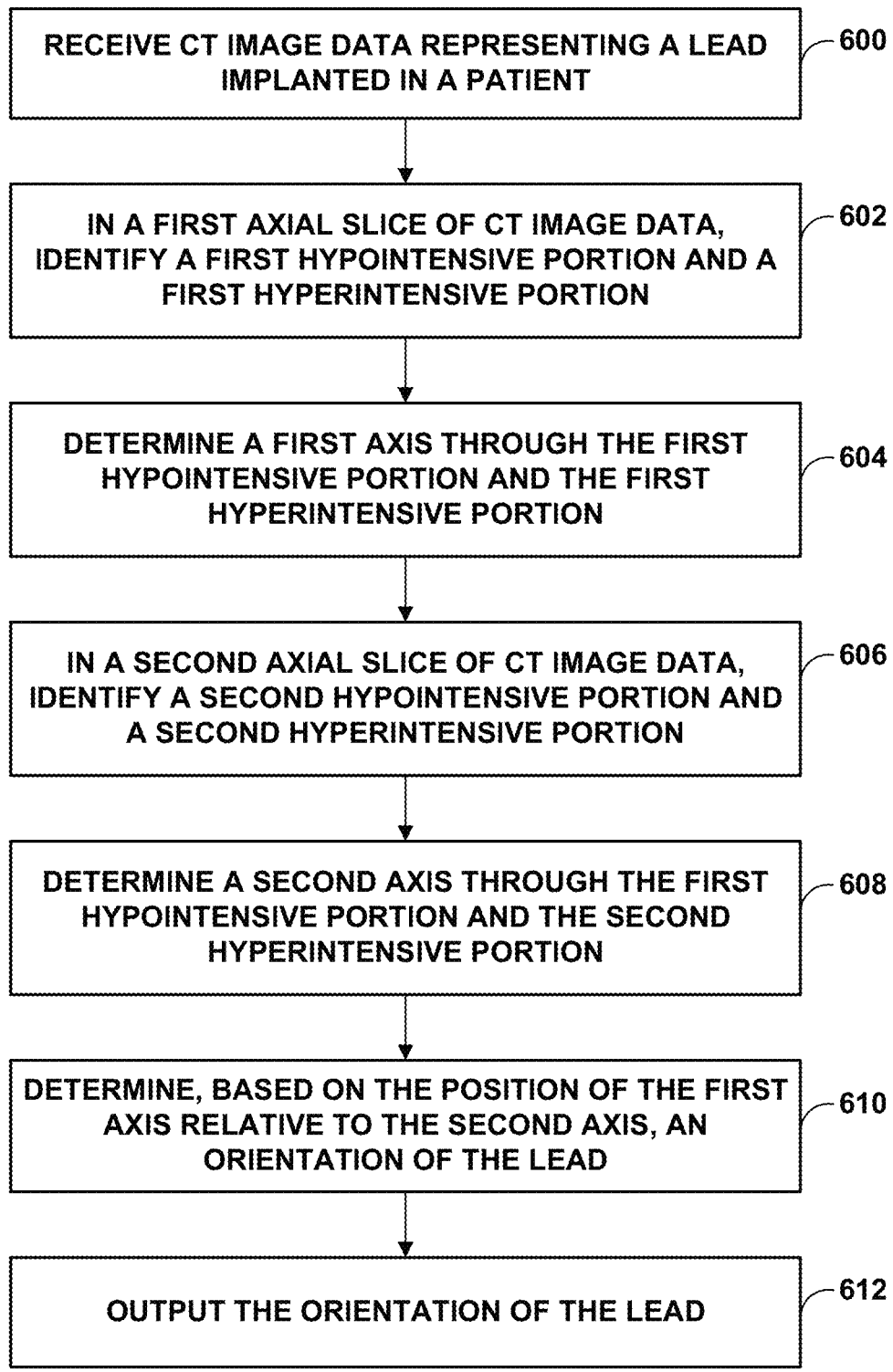
FIG. 12 is a flow diagram illustrating an example technique for determining the orientation of a lead implanted in a patient based on multiple axial slices of image data, in accordance with one or more techniques of this disclosure.

FIG. 12 is a flow diagram illustrating an example technique for determining the orientation of a lead implanted in a patient based on multiple axial slices of image data, in accordance with one or more techniques of this disclosure. For purposes of explanation, the technique of FIG. 12 will be described with respect to lead detection system 102 of FIGS. 1 and 10. However, lead detection systems other than lead detection system 102 may perform some or all of the technique of FIG. 12.

In the example of FIG. 12, lead detection system 102 receives or otherwise obtains CT image data representing a lead implanted in a patient (500). For instance, communication module 442 of lead detection system 102 may obtain, from imaging device 100, computed tomography (CT) images of patient 40 of FIG. 1 of a region of patient 40 in which lead 50 is implanted. As discussed above, example formats of the image data include, but are not necessarily limited to, Analyze, Neuroimaging Informatics Technology Initiative (Nifti), Minc, and Digital Imaging and Communications in Medicine (DICOM).

Lead detection system 102 then obtains a first axial slice of CT image data and identifies, in a first axial slice of the CT image data, a first hypointensive portion and a first hyperintensive portion (602). For example, lead detection system 102 may apply a hypointensive threshold to the CT image data to determine all voxels below the hypointensive threshold and apply a hyperintensive threshold to the CT image data to determine all voxels exceeding the hyperintensive threshold. Lead detection system 102 then determines a first axis through the first hypointensive portion and the first hyperintensive portion (604). In some examples, as shown in FIG. 8A, lead detection system 102 determines the first axis through two hyperintensive portions.

Lead detection system 102 then obtains a second axial slice of CT image data and identifies, in the second axial slice of the CT image data, a second hypointensive portion and a second hyperintensive portion (606). For example, lead detection system 102 may apply a hypointensive threshold to the CT image data to determine all voxels below the hypointensive threshold and apply a hyperintensive threshold to the CT image data to determine all voxels exceeding the hyperintensive threshold. Lead detection system 102 then determines a second axis through the second hypointensive portion and the second hyperintensive portion (608). In some examples, as shown in FIG. 8B, lead detection system 102 determines the second axis through two hyperintensive portions.

Lead detection system 102 then determines, based on the position of the first axis relative to the second axis, the orientation of lead 50 (610). The first axis and the second axis provide orientations of the respective orientation markers 82, for example. Although each orientation marker may be disposed on either side of the respective axis, the orientation markers 82 may be positioned at a non-orthogonal angle with respect to each other. Therefore, in one example, lead detection system 102 can determine the angle between the first and second axes to determine the specific orientation of the orientation markers and thus the entire lead 50.

Lead detection system 102 also outputs the determined orientation of lead 50 (612). For example, lead detection system 102 may transmit the orientation to programmer 30 to facilitate stimulation parameter selection for therapy or output, for display, a graphical representation of the orientation of the lead, and electrodes, with respect to patient 40. Lead detection system 102 may output an indication of the determined rotational orientation. For instance, lead detection module 140 may be executable by processor 124 to cause output device 444 to display a graphical representation of the lead overlaid on an image of the patient in which the lead is implanted. The graphical representation may show the orientation and/or location of the lead relative to the patient. As another example, lead detection module 440 may cause output device 444 to display numerical representations of any combination of the outputs described above (e.g., centroid of distal electrode, direction of lead trajectory, direction of the center of the target electrode segment).

A practitioner may utilize the determined rotational orientation of the lead to program (e.g., using programmer 30) operation of IMD 20. For instance, where it is desirable to deliver electrical stimulation therapy to a particular volume of the patient's brain (e.g., a specific volume of activation), the practitioner may use programmer 30 to program IMD 30 to deliver electrical stimulation therapy via electrodes of lead 50 that activate the particular volume. In other examples, programmer 30 or another device may automatically select stimulation parameters based on the rotational orientation of lead 50.

Figure 13:
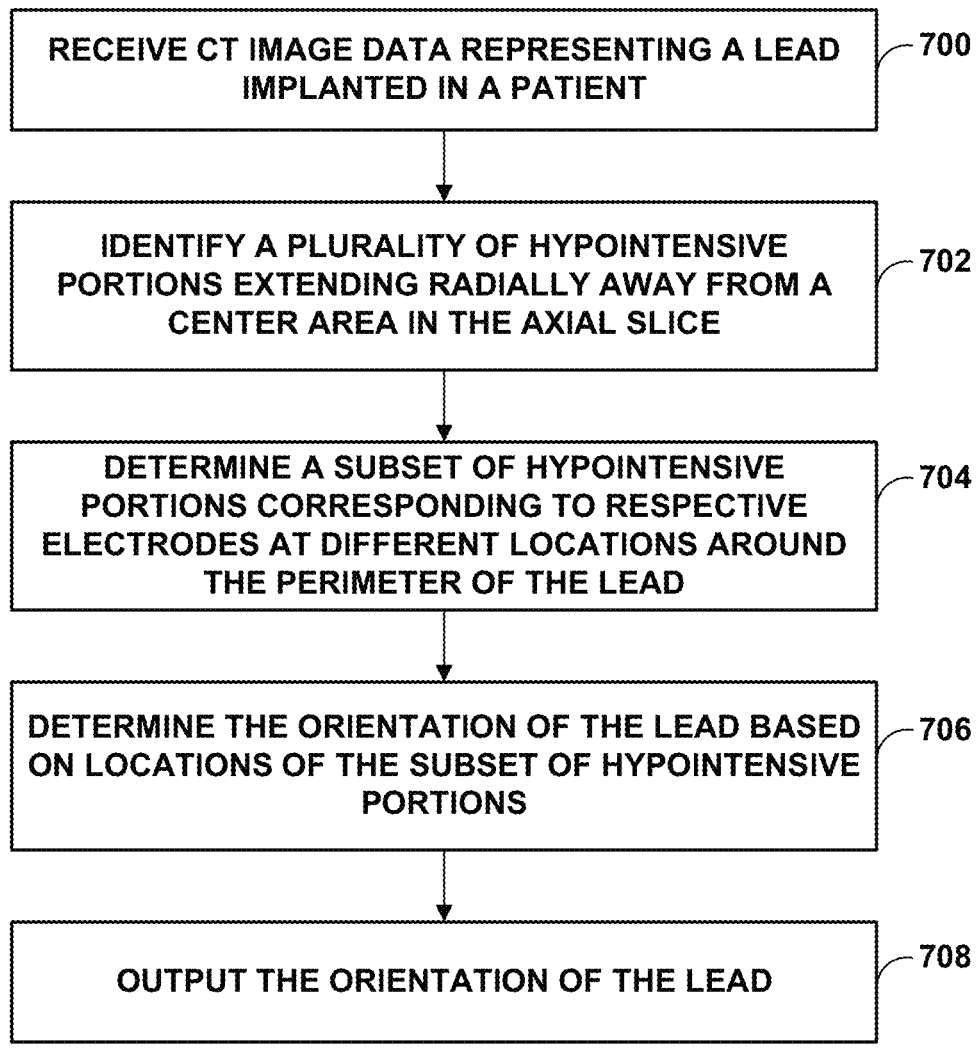
FIG. 13 is a flow diagram illustrating an example technique for determining the orientation of a lead implanted in a patient based on a plurality of hypointensive portions in an axial slice of image data, in accordance with one or more techniques of this disclosure.

FIG. 13 is a flow diagram illustrating an example technique for determining the orientation of a lead implanted in a patient based on a plurality of hypointensive portions in an axial slice of image data corresponding to electrodes of the lead. For purposes of explanation, the technique of FIG. 13 will be described with respect to lead detection system 102 of FIGS. 1 and 10. However, lead detection systems other than lead detection system 102 may perform some or all of the technique of FIG. 11.

In the example of FIG. 13, lead detection system 102 receives or otherwise obtains CT image data representing a lead implanted in a patient (700). For instance, communication module 442 of lead detection system 102 may obtain, from imaging device 100, computed tomography (CT) images of patient 40 of FIG. 1 of a region of patient 40 in which lead 50 is implanted. As discussed above, example formats of the image data include, but are not necessarily limited to, Analyze, Neuroimaging Informatics Technology Initiative (Nifti), Minc, and Digital Imaging and Communications in Medicine (DICOM).

Lead detection system 102 then identifies a plurality of hypointensive portions extending radially away from a center area in the axial slice of the CT image data (702). For example, lead detection system 102 may apply a hypointensive threshold to the CT image data to determine all voxels below the hypointensive threshold. Lead detection system 102 may not specifically identify the center area in some examples, but the hypointensive portions would extend from a center area that would correspond to the lead location. In some examples, lead detection system 102 may identify the hyperintensive portion at the location of the lead to identify the center area. Lead detection system 102 then determines a subset of hypointensive portions corresponding to the respective electrodes at different locations around the perimeter of lead 50 (704). For example, lead detection system 102 may identify one or more characteristics of the hyperintensive portions that indicate the location of an electrode. One characteristic may be a wider hypointensive portion and/or shorter hypointensive portions corresponding to the electrode location, or another characteristic may be longer hypointensive portions corresponding to the gaps between electrodes. These characteristics that distinguish electrodes from the gaps between electrodes may be dependent on the size, shape, material, or any other features of the electrodes of lead 50.

Lead detection system 102 then determines, based on the locations of the subset of hypointensive portions, the orientation of lead 50 implanted within the patient (706). Lead detection system 102 also outputs the determined orientation of lead 50 (708). For example, lead detection system 102 may transmit the orientation to programmer 30 to facilitate stimulation parameter selection for therapy or output, for display, a graphical representation of the orientation of the lead, and electrodes, with respect to patient 40. In some examples, lead detection system 102 may use the determined locations of electrodes according to the technique of FIG. 13 to confirm the orientation of the lead according to the position of orientation markers as described herein. In other examples, lead detection system 102 may determine where the electrodes are located according to FIG. 13, and then identify which electrodes are located at each electrode location by sensing physiological signals or sensing other signals generated by other electrodes.

While the techniques described above are primarily described as being performed by processor 424 of lead detection system 102, in other examples, one or more other processors may perform any part of the techniques described herein alone or in addition to processor 424. Thus, reference to "a processor" may refer to "one or more processors." Likewise, "one or more processors" may refer to a single processor or multiple processors in different examples.

The techniques described in this disclosure, including those attributed to lead detection system 102 or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

The following numbered examples may illustrate one or more aspects of this disclosure. Example 1: A system includes processing circuitry configured to: receive computed image data representing a lead implanted within a patient; identify, from the image data, at least one hypointensive portion; identify, from the image data, at least one hyperintensive portion; determine, based on the at least one hypointensive portion and the at least one hyperintensive portion, an orientation of the lead within the patient; and output the orientation of the lead.

Example 2: The system of example 1, wherein the processing circuitry is configured to identify the at least one hypointensive portion and the at least one hyperintensive portion from an axial slice of the image data corresponding to an axial location of at least one orientation marker of the lead.

Example 3: The system of any of examples 1 and 2, wherein the processing circuitry is configured to: determine an axis through the at least one hypointensive portion and the at least one hyperintensive portion; and determine the orientation of the lead based on a position of the axis with respect to the image data.

Example 4: The system of example 3, wherein the axis comprises a first axis, the at least one hypointensive portion comprises a first hypointensive portion, and the at least one hyperintensive portion comprises a first hyperintensive portion, wherein the image data comprises a first axial slice includes identify, from a second axial slice of the image data different than the first axial slice, a second hypointensive portion; identify, from the second axial slice of the image data, a second hyperintensive portion; determine a second axis through the second hypointensive portion and the second hyperintensive portion, wherein the first axis and the second axis have different orientations with respect to the lead; and determine the orientation of the lead based on a position of the first axis in the first axial slice relative to the position of the second axis in the second axial slice.

Example 5: The system of any of examples 1 through 4, wherein the processing circuitry is configured to: identify the at least one hypointensive portion by identifying a first hypointensive portion and a second hypointensive portion;

the hyperintensive disposed between the first hypointensive portion and the second hypointensive portion; and determine, based on a position of the first hypointensive portion and the second hypointensive portion with respect to the hyperintensive portion, the orientation of the lead.

Example 6: The system of any of examples 1 through 5, wherein the at least one hypointensive portion is indicative of at least one orientation marker of the lead, and wherein the at least one hyperintensive portion is representative of the lead.

Example 7: The system of any of examples 1 through 6, wherein the at least one orientation marker comprises an asymmetrical shape.

Example 8: The system of any of examples 1 through 7, wherein the at least one hypointensive portion comprises a plurality of hypointensive portions, and wherein the processing circuitry is configured to: identify each hypointensive portion of the plurality of hypointensive portions extending away from the at least one hyperintensive portion in an axial slice of the image data; and determine a subset of hypointensive portions of the plurality of hypointensive portions that correspond to respective electrodes at different respective positions around a perimeter of the lead, wherein the processing circuitry is configured to determine the orientation of the lead based on locations of the subset of hypointensive portions.

Example 9: The system of any of examples 1 through 8, wherein the processing circuitry is configured to: identify the at least one hypointensive portion by determining first voxels of the image data having a first intensity below a hypointensive threshold; and identify the at least one hyperintensive portion by determining second voxels of the image data having a second intensity exceeding a hyperintensive threshold.

Example 10: The system of any of examples 1 through 9, further comprising a display, wherein the processing circuitry is configured to output, for presentation on the display, the orientation of the lead.

Example 11: The system of any of examples 1 through 10, wherein the image data comprises computed tomography (CT) image data.

Example 12: A method that includes receiving image data representing a lead implanted within a patient; identifying, from the image data, at least one hypointensive portion; identifying, from the image data, at least one hyperintensive portion; determining, based on the at least one hypointensive portion and the at least one hyperintensive portion, an orientation of the lead within the patient; and outputting the orientation of the lead.

Example 13: The method of example 12, wherein to identifying the at least one hypointensive portion and the at least one hyperintensive portion comprises identifying the at least one hypointensive portion and the at least one hyperintensive portion from an axial slice of the image data corresponding to an axial location of at least one orientation marker of the lead.

Example 14: The method of any of examples 12 and 13, further includes determining an axis through the at least one hypointensive portion and the at least one hyperintensive portion, and wherein determining the orientation of the lead comprises determining the orientation of the lead based on a position of the axis with respect to the image data.

Example 15: The method of example 14, wherein the axis comprises a first axis, the at least one hypointensive portion comprises a first hypointensive portion, and the at least one hyperintensive portion comprises a first hyperintensive portion, wherein the image data comprises a first axial slice includes identifying, from a second axial slice of the image data different than the first axial slice, a second hypointensive portion; identifying, from the second axial slice of the image data, a second hyperintensive portion; determining a second axis through the second hypointensive portion and the second hyperintensive portion, wherein the first axis and the second axis have different orientations with respect to the lead, and wherein determining the orientation of the lead comprises determining the orientation of the lead based on a position of the first axis in the first axial slice relative to the position of the second axis in the second axial slice.

Example 16: The method of any of examples 12 through 15, wherein: identifying at least one hypointensive portion comprises identifying a first hypointensive portion and a second hypointensive portion; the hyperintensive disposed between the first hypointensive portion and the second hypointensive portion, and determining the orientation of the lead comprises determining, based on a position of the first hypointensive portion and the second hypointensive portion with respect to the hyperintensive portion, the orientation of the lead.

Example 17: The method of any of examples 12 through 16, wherein the at least one hypointensive portion is indicative of at least one orientation marker of the lead, and wherein the at least one hyperintensive portion is representative of the lead.

Example 18: The method of any of examples 12 through 17, wherein the at least one orientation marker comprises an asymmetrical shape.

Example 19: The method of any of examples 12 through 18, wherein the at least one hypointensive portion comprises a plurality of hypointensive portions, and wherein the method further comprises: identifying each hypointensive portion of the plurality of hypointensive portions extending away from the at least one hyperintensive portion in an axial slice of the image data; and determining a subset of hypointensive portions of the plurality of hypointensive portions that correspond to respective electrodes at different respective positions around a perimeter of the lead, and wherein determining the orientation of the lead comprises determining the orientation of the lead based on locations of the subset of hypointensive portions.

Example 20: The method of any of examples 12 through 19, wherein: identifying the at least one hypointensive portion comprises determining first voxels of the image data having a first intensity below a hypointensive threshold; and identifying the at least one hyperintensive portion comprises determining second voxels of the image data having a second intensity exceeding a hyperintensive threshold.

Example 21: The method of any of examples 12 through 20, further comprising outputting, for presentation on a display, the orientation of the lead.

Example 22: The method of any of examples 12 through 21, wherein the image data comprises computed tomography (CT) image data.

Example 23: A computer-readable storage medium storing instructions that, when executed, cause processing circuitry to: receive image data representing a lead implanted within a patient; identify, from the image data, at least one hypointensive portion; identify, from the image data, at least one hyperintensive portion; determine, based on the at least one hypointensive portion and the at least one hyperintensive portion, an orientation of the lead within the patient; and output the orientation of the lead.

Example 24: The computer-readable storage medium of example 23, wherein the at least one hypointensive portion comprises a first hypointensive portion, the at least one hyperintensive portion comprises a first hyperintensive portion, and the image data comprises a first axial slice includes determine a first axis through the first hypointensive portion and the at least one hyperintensive portion in the first axial slice; identify, from a second axial slice of the image data different than the first axial slice, a second hypointensive portion; identify, from the second axial slice of the image data, a second hyperintensive portion; determine a second axis through the second hypointensive portion and the second hyperintensive portion, wherein the first axis and the second axis have different orientations with respect to the lead; and determine the orientation of the lead based on a position of the first axis in the first axial slice relative to the position of the second axis in the second axial slice.

Example 25: The computer-readable storage medium of any of examples 23 and 24, wherein the image data comprises computed tomography (CT) image data.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples of the disclosure have been described. These and other embodiments are within the scope of the following claims.

What is claimed is:

1. A system comprising:
processing circuitry configured to:
receive computed image data representing a lead implanted within a patient;
identify, from the image data, at least one hypointensive portion by at least determining first voxels or pixels of the image data having a first intensity below a hypointensive threshold;
identify, from the image data, at least one hyperintensive portion by at least determining second voxels or pixels of the image data having a second intensity exceeding a hyperintensive threshold;
determine, based on the at least one hypointensive portion and the at least one hyperintensive portion, an orientation of the lead within the patient; and
output the orientation of the lead.

2. The system of claim 1, wherein the processing circuitry is configured to identify the at least one hypointensive portion and the at least one hyperintensive portion from an axial slice of the image data corresponding to an axial location of at least one orientation marker of the lead.

3. The system of claim 1, wherein the processing circuitry is configured to:
determine an axis through the at least one hypointensive portion and the at least one hyperintensive portion; and
determine the orientation of the lead based on a position of the axis with respect to the image data.

4. The system of claim 3, wherein the axis comprises a first axis, the at least one hypointensive portion comprises a first hypointensive portion, and the at least one hyperintensive portion comprises a first hyperintensive portion, wherein the image data comprises a first axial slice comprising the first hypointensive portion and the first hyperintensive portion, and wherein the processing circuitry is configured to:
identify, from a second axial slice of the image data different than the first axial slice, a second hypointensive portion;
identify, from the second axial slice of the image data, a second hyperintensive portion;
determine a second axis through the second hypointensive portion and the second hyperintensive portion, wherein the first axis and the second axis have different orientations with respect to the lead; and
determine the orientation of the lead based on a position of the first axis in the first axial slice relative to the position of the second axis in the second axial slice.

5. The system of claim 1, wherein the processing circuitry is configured to:
identify the at least one hypointensive portion by identifying a first hypointensive portion and a second hypointensive portion; the hyperintensive portion disposed between the first hypointensive portion and the second hypointensive portion; and
determine, based on a position of the first hypointensive portion and the second hypointensive portion with respect to the hyperintensive portion, the orientation of the lead.

6. The system of claim 1, wherein the at least one hypointensive portion is indicative of at least one orientation marker of the lead, and wherein the at least one hyperintensive portion is representative of the lead.

7. The system of claim 1, wherein the at least one orientation marker comprises an asymmetrical shape.

8. The system of claim 1, wherein the at least one hypointensive portion comprises a plurality of hypointensive portions, and wherein the processing circuitry is configured to:
  identify each hypointensive portion of the plurality of hypointensive portions extending away from the at least one hyperintensive portion in an axial slice of the image data; and
  determine a subset of hypointensive portions of the plurality of hypointensive portions that correspond to respective electrodes at different respective positions around a perimeter of the lead, wherein the processing circuitry is configured to determine the orientation of the lead based on locations of the subset of hypointensive portions.

9. The system of claim 1, wherein the processing circuitry is configured to:
  identify the at least one hypointensive portion by at least determining the first voxels of the image data having the first intensity below the hypointensive threshold; and
  identify the at least one hyperintensive portion by determining the second voxels of the image data having the second intensity exceeding the hyperintensive threshold.

10. The system of claim 1, further comprising a display, wherein the processing circuitry is configured to output, for presentation on the display, the orientation of the lead.

11. The system of claim 1, wherein the image data comprises computed tomography (CT) image data.

12. A method comprising:
  receiving image data representing a lead implanted within a patient;
  identifying, from the image data, at least one hypointensive portion by at least determining first voxels or pixels of the image data having a first intensity below a hypointensive threshold;
  identifying, from the image data, at least one hyperintensive portion by at least determining second voxels or pixels of the image data having a second intensity exceeding a hyperintensive threshold;
  determining, based on the at least one hypointensive portion and the at least one hyperintensive portion, an orientation of the lead within the patient; and
  outputting the orientation of the lead.

13. The method of claim 12, wherein to identifying the at least one hypointensive portion and the at least one hyperintensive portion comprises identifying the at least one hypointensive portion and the at least one hyperintensive portion from an axial slice of the image data corresponding to an axial location of at least one orientation marker of the lead.

14. The method of claim 12, further comprising:
  determining an axis through the at least one hypointensive portion and the at least one hyperintensive portion, and wherein determining the orientation of the lead comprises determining the orientation of the lead based on a position of the axis with respect to the image data.

15. The method of claim 14, wherein the axis comprises a first axis, the at least one hypointensive portion comprises a first hypointensive portion, and the at least one hyperintensive portion comprises a first hyperintensive portion, wherein the image data comprises a first axial slice comprising the first hypointensive portion and the first hyperintensive portion, and wherein the method further comprises:
  identifying, from a second axial slice of the image data different than the first axial slice, a second hypointensive portion;
  identifying, from the second axial slice of the image data, a second hyperintensive portion;
  determining a second axis through the second hypointensive portion and the second hyperintensive portion, wherein the first axis and the second axis have different orientations with respect to the lead, and wherein determining the orientation of the lead comprises determining the orientation of the lead based on a position of the first axis in the first axial slice relative to the position of the second axis in the second axial slice.

16. The method of claim 12, wherein:
  identifying at least one hypointensive portion comprises identifying a first hypointensive portion and a second hypointensive portion; the hyperintensive portion disposed between the first hypointensive portion and the second hypointensive portion, and
  determining the orientation of the lead comprises determining, based on a position of the first hypointensive portion and the second hypointensive portion with respect to the hyperintensive portion, the orientation of the lead.

17. The method of claim 12, wherein the at least one hypointensive portion is indicative of at least one orientation marker of the lead, and wherein the at least one hyperintensive portion is representative of the lead.

18. The method of claim 12, wherein the at least one orientation marker comprises an asymmetrical shape.

19. The method of claim 12, wherein the at least one hypointensive portion comprises a plurality of hypointensive portions, and wherein the method further comprises:
  identifying each hypointensive portion of the plurality of hypointensive portions extending away from the at least one hyperintensive portion in an axial slice of the image data; and
  determining a subset of hypointensive portions of the plurality of hypointensive portions that correspond to respective electrodes at different respective positions around a perimeter of the lead, and wherein determining the orientation of the lead comprises determining the orientation of the lead based on locations of the subset of hypointensive portions.

20. The method of claim 12, wherein:
  identifying the at least one hypointensive portion comprises determining the first voxels of the image data having the first intensity below the hypointensive threshold; and
  identifying the at least one hyperintensive portion comprises determining the second voxels of the image data having the second intensity exceeding the hyperintensive threshold.

21. The method of claim 12, further comprising outputting, for presentation on a display, the orientation of the lead.

22. The method of claim 12, wherein the image data comprises computed tomography (CT) image data.

23. A non-transitory computer-readable storage medium storing instructions that, when executed, cause processing circuitry to:
  receive image data representing a lead implanted within a patient;
  identify, from the image data, at least one hypointensive portion by at least determining first voxels or pixels of the image data having a first intensity below a hypointensive threshold;

identify, from the image data, at least one hyperintensive portion by at least determining second voxels or pixels of the image data having a second intensity exceeding a hyperintensive threshold;

determine, based on the at least one hypointensive portion and the at least one hyperintensive portion, an orientation of the lead within the patient; and output the orientation of the lead.

24. The non-transitory computer-readable storage medium of claim 23, wherein the at least one hypointensive portion comprises a first hypointensive portion, the at least one hyperintensive portion comprises a first hyperintensive portion, and the image data comprises a first axial slice comprising the first hypointensive portion and the first hyperintensive portion, and wherein computer-readable storage medium further comprises instructions that, when executed, cause the processing circuitry to:

determine a first axis through the first hypointensive portion and the at least one hyperintensive portion in the first axial slice;

identify, from a second axial slice of the image data different than the first axial slice, a second hypointensive portion;

identify, from the second axial slice of the image data, a second hyperintensive portion;

determine a second axis through the second hypointensive portion and the second hyperintensive portion, wherein the first axis and the second axis have different orientations with respect to the lead; and determine the orientation of the lead based on a position of the first axis in the first axial slice relative to the position of the second axis in the second axial slice.

25. The non-transitory computer-readable storage medium of claim 23, wherein the image data comprises computed tomography (CT) image data.

* * * * *